United States Patent
Murade et al.

(10) Patent No.: US 11,242,555 B2
(45) Date of Patent: Feb. 8, 2022

(54) MOLECULAR SENSORS AND USES THEREOF

(71) Applicant: New York University, New York, NY (US)

(72) Inventors: Chandrashekhar Uttamrao Murade, Abu Dhabi (AE); George Shubeita, Abu Dhabi (AE)

(73) Assignee: New York University, New York, NY (US)

( * ) Notice: Subject to any disclaimer, the term of this patent is extended or adjusted under 35 U.S.C. 154(b) by 0 days.

(21) Appl. No.: 16/584,014

(22) Filed: Sep. 26, 2019

(65) Prior Publication Data
US 2020/0095627 A1 Mar. 26, 2020

Related U.S. Application Data

(60) Provisional application No. 62/736,812, filed on Sep. 26, 2018.

(51) Int. Cl.
*C12Q 1/6818* (2018.01)
*C12Q 1/6862* (2018.01)
*G01N 21/64* (2006.01)

(52) U.S. Cl.
CPC ......... *C12Q 1/6818* (2013.01); *C12Q 1/6862* (2013.01); *G01N 21/6408* (2013.01); *G01N 21/6428* (2013.01); *G01N 2021/6441* (2013.01)

(58) Field of Classification Search
CPC ............... C12Q 1/6818; C12Q 1/6862; G01N 21/6428; G01N 21/6408; G01N 2021/6441
See application file for complete search history.

(56) References Cited

U.S. PATENT DOCUMENTS

| | | | | |
|---|---|---|---|---|
| 6,544,746 B2* | 4/2003 | Heyduk | ............... | G01N 33/542 435/18 |
| 2003/0027799 A1* | 2/2003 | Jolivet | ................... | A61K 33/24 514/87 |
| 2010/0216249 A1* | 8/2010 | Kapanidis | ................ | C12Q 1/68 436/86 |
| 2012/0021410 A1* | 1/2012 | Yin | .......................... | C07K 1/13 435/6.1 |
| 2012/0288857 A1* | 11/2012 | Livak | ................... | C12Q 1/6823 435/6.11 |

OTHER PUBLICATIONS

Chiu et al, Genome-wide prediction of minor-groove electrostatic potential enables biophysical modeling of protein-DNA binding, 2017, Nucleic Acids Research, 45, 12565-12576 (Year: 2017).*
Dasari et al, Cisplatin in cancer therapy: Molecular mechanisms of action, 2014, 740, 364-378. (Year: 2014).*
Murade et al, A Molecular Sensor Reveals Differences in Macromolecular Crowding between the Cytoplasm and Nucleoplasm, 2019, (Post Art), ACS Sens. 4, 1835-1843 (Year: 2019).*

* cited by examiner

*Primary Examiner* — Narayan K Bhat
(74) *Attorney, Agent, or Firm* — Hodgson Russ LLP

(57) ABSTRACT

The present disclosure provides molecular sensors. The molecular sensors may be flexible or linear and are oligonucleotide-based and have fluorescent groups. The molecular sensors may be used in methods to measure molecular crowding, identify of binding modes of various substrates, pharmaceutical drug screens, and in high-throughput methods.

8 Claims, 30 Drawing Sheets

MOLECULAR SENSORS AND USES THEREOF

CROSS REFERENCE TO RELATED APPLICATIONS

This application claims priority to U.S. Provisional Application No. 62/736,812, filed on Sep. 26, 2018, the disclosure of which is incorporated by reference herein.

FIELD OF THE DISCLOSURE

The disclosure generally relates to molecular sensors. More particularly the disclosure relates to oligonucleotide-based molecular sensors for detecting macromolecular crowding and binding.

BACKGROUND OF THE DISCLOSURE

Many molecular species (small molecules and proteins) bind to DNA and in doing so modify DNA structure. These structural changes are often part of the normal cellular function, but are sometimes aberrant modifications due to endogenous and exogenous factors and can lead to mutations or cell replication defects. Taking advantage of these mechanisms, drugs that bind and alter DNA are also often used in cancer treatments or as antibiotics to stop cell proliferation.

The induced change in DNA structure upon complexing with the drug prevents polymerase and other DNA binding proteins from functioning properly. DNA synthesis and transcription are consequently impaired leading to cancer cell death, for example. A class of these drugs—intercalators—wedge between the DNA bases resulting in DNA extension and deformation. Another class of drugs—groove binders—attach to the DNA double helix grooves and modify its surface and interfere with protein-DNA interactions.

There is a need for a sensor and/or method that allows for the rapid and direct detection of DNA conformational changes, which is compatible with living cells to study molecule-DNA interaction and in pharmaceutical screens for novel drugs that target DNA.

SUMMARY OF THE DISCLOSURE

The present disclosure provides molecular sensors and methods of using same. Molecular sensors of the present disclosure are oligonucleotide molecules (e.g., DNA, RNA, PNA, and the like) that bind substrates (e.g., small molecules, proteins, and the like). Molecular sensors of the present disclosure can be flexible molecular sensors or linear molecular sensors. The molecular sensors and methods of the present disclosure directly detect the binding (e.g., through intercalation, major groove binding, minor groove binding, electrostatic binding, and the like) of substrates to the oligonucleotides even if the substrate is not fluorescent, and further provide a quantitative measure of stoichiometry.

In an aspect, a molecular sensor of the present disclosure is a flexible molecular sensor.

A flexible molecular sensor of the present disclosure comprises a first double-stranded oligonucleotide (e.g., DNA, RNA, PNA, and the like, and combinations thereof, such as, for example, a DNA-RNA hybrid, more than two DNA strands hybridized using DNA origami methods as known in the art) arm, a second double-stranded oligonucleotide (e.g., DNA, RNA, PNA, and the like, and combinations thereof, such as, for example, a DNA-RNA hybrid, more than two DNA strands hybridized using DNA origami methods) arm, and a linking moiety (e.g., a flexible linking moiety). The linking moiety (e.g., a flexible linking moiety) connects (e.g., is covalently bonded to) the first double-stranded oligonucleotide arm at one strand of the first double-stranded arm and to the second double-stranded oligonucleotide arm at one strand of the second double-stranded arm. Each double-stranded oligonucleotide arm further comprises a fluorescent group (e.g., a group derived from a fluorescent molecule) that are attached (e.g., covalently bonded, non-covalently bound through, such as, for example, biotin-avidin binding) to each arm, such that the fluorescent groups or derivatives thereof may interact. In an example, the first double-stranded oligonucleotide arm has a first fluorescent group (e.g., a group derived from a fluorescent molecule, such as, for example, a donor chromophore or a group derived therefrom) and the second double-stranded oligonucleotide arm has a second fluorescent group (e.g., a group derived from a fluorescent molecule, such as, for example, an acceptor chromophore or a group derived therefrom), where the first fluorescent group or derivative thereof and the second fluorescent group or derivative thereof are positioned such that the first fluorescent group or derivative thereof and the second fluorescent group or derivative thereof can interact with each other (e.g., exhibit a change in Fluorescence Resonance Energy Transfer (FRET) efficiency as the first fluorescent group or derivative thereof and the second fluorescent group or derivative thereof are spatially separated).

In an aspect, the present disclosure provides linear molecular sensors.

In an example, the linear molecular sensor of the present disclosure comprises a double-stranded oligonucleotide (e.g., DNA, RNA, PNA, and the like). Each 5' end is labelled with a fluorescent group or derivative thereof (e.g., a first fluorescent group or derivative thereof, such as, for example, a donor chromophore or derivative thereof and a second fluorescent group or derivative thereof, such as, for example, an acceptor chromophore or derivative thereof). Such a sensor is depicted in FIGS. 15 and 21.

In an aspect, the present disclosure provides methods for using molecular sensors of the present disclosure (e.g., linear and/or flexible molecular sensors of the present disclosure). Methods of the present disclosure involve determining binding of at least one substrate (e.g., at least one small molecule, at least one protein, and the like, and combinations thereof). Additionally, methods of the present disclosure comprise determining molecular crowding.

In an example, a method of the present disclosure for detecting binding of at least one substrate (e.g., at least one small molecule, at least one protein, and the like, and combinations thereof) comprises: i) contacting in a medium (e.g., an aqueous medium) the at least one substrate with a molecular sensor of the present disclosure (e.g., flexible molecular sensor or linear molecular sensor) or a composition of the present disclosure; ii) measuring a change (i.e., increase or decrease) in fluorescence of molecular sensor of the present disclosure or a composition of the present disclosure relative to a reference fluorescent value of the molecular sensor of the present disclosure or composition of the present disclosure in the absence of the substrate, where the change in fluorescence is indicative of binding of the substrate to the molecular sensor. Binding may be an intercalation binding event, a major groove binding event, a minor groove binding event, a covalent binding event, an electrostatic binding event, or a combination thereof.

In an example, a method of the present disclosure is performed on a test sample comprising an analyte of interest (e.g., a test sample containing a substrate, such as, for example, a small molecule drug, peptide, and/or the like).

In an example, a method of the present disclosure involves determining if a substrate has reached an organelle or cellular structure of interest. Such a method in cell culture comprises: i) transfecting the cells with a sensor of the present disclosure; ii) imaging before and after introduction of a molecule of interest (e.g., a drug) that is being tested for oligonucleotide (e.g., DNA) binding within the cells. If the molecule of interest (e.g., a drug) penetrates the cell membrane, it will bind to the sensor, and the binding would be detected via a change in the fluorescence of the sensor. Because the sensor is distributed throughout the cell, the molecule of interest (e.g., drug) reaching various cellular compartments (e.g., cell nucleus) in real time. Additionally, the amount of time taken for a particular molecule of interest (e.g., a drug) to reach particular compartment can be measured. Information on the uptake and distribution of a molecule of interest can be determined by imaging the sensor of the present disclosure within a cell as the sensor interacts with a molecule of interest (e.g., a drug).

In an example, a method of the present disclosure is be used to measure molecular crowding (e.g., macromolecular crowding). Macromolecular crowding occurs when a large fraction of the volume of a solution is taken up by macromolecules. This has an effect of reducing the available volume in the solution which can result in, such as, for example the following: changes in the conformation of macromolecules (more compact structures would often be favored), altering the binding kinetics between molecules, and the like. For example, when using the flexible molecular sensor of the present disclosure, the more closed it is the more compact it is and therefore putting the sensor in a crowded solution favors a more closed conformation of the sensor. A closed conformation in turn brings the fluorophores closer to each other, therefore increasing the efficiency of energy transfer. Binding may not occur in a method to measure molecular crowding; however, weak binding may occurring depending on the molecular species involved.

In an aspect, the present disclosure provides administering a compound to an individual in need of treatment, where the compound is an intercalator, major groove binder, minor groove binder, covalent binder, electrostatic binder, or the like, or a combination thereof.

In an aspect, the present disclosure provides methods of identifying substrates having a particular mode of binding (e.g., intercalation, major groove, minor groove, covalent, electrostatic, and the like, and combinations thereof). The substrates having a particular mode of binding may then be used for treatment of conditions where other therapeutic agents exhibit the same mode of binding are known to be useful. For example, a substrate identified as an intercalator by a method of the present disclosure may be suitable to treat a condition where other known therapies comprise administering intercalating compounds. Identification may be carried in in a high throughput method, such as, for example, using a fluorescence plate reader and a multiwell plate (e.g., a 96-well plate, a 384-well plate, and the like).

In an example, a method of treating with a compound (e.g., an identified compound) having a particular mode of binding comprises a) identifying the particular mode of binding of a compound (e.g., a substrate) by i) contacting in a medium (e.g., an aqueous medium) the at least one substrate with a molecular sensor of the present disclosure (e.g., flexible molecular sensor or linear molecular sensor) or a composition of the present disclosure; ii) measuring a change (i.e., increase or decrease) in fluorescence of molecular sensor of the present disclosure or a composition of the present disclosure relative to a reference fluorescent value of the molecular sensor of the present disclosure or composition of the present disclosure in the absence of the substrate, where the change in fluorescence is indicative of binding of the substrate to the molecular sensor, where the mode of binding may be determined based on the type of molecular sensor used (e.g., flexible molecular sensor or linear molecular sensor); b) administering a therapeutically effective amount of the identified compound to an individual in need of treatment having a condition where other therapeutic agents that exhibit the same mode of binding are known to be useful.

BRIEF DESCRIPTION OF THE FIGURES

For a fuller understanding of the nature and objects of the disclosure, reference should be made to the following detailed description taken in conjunction with the accompanying figures.

DETAILED DESCRIPTION OF THE DISCLOSURE

Figure 1:
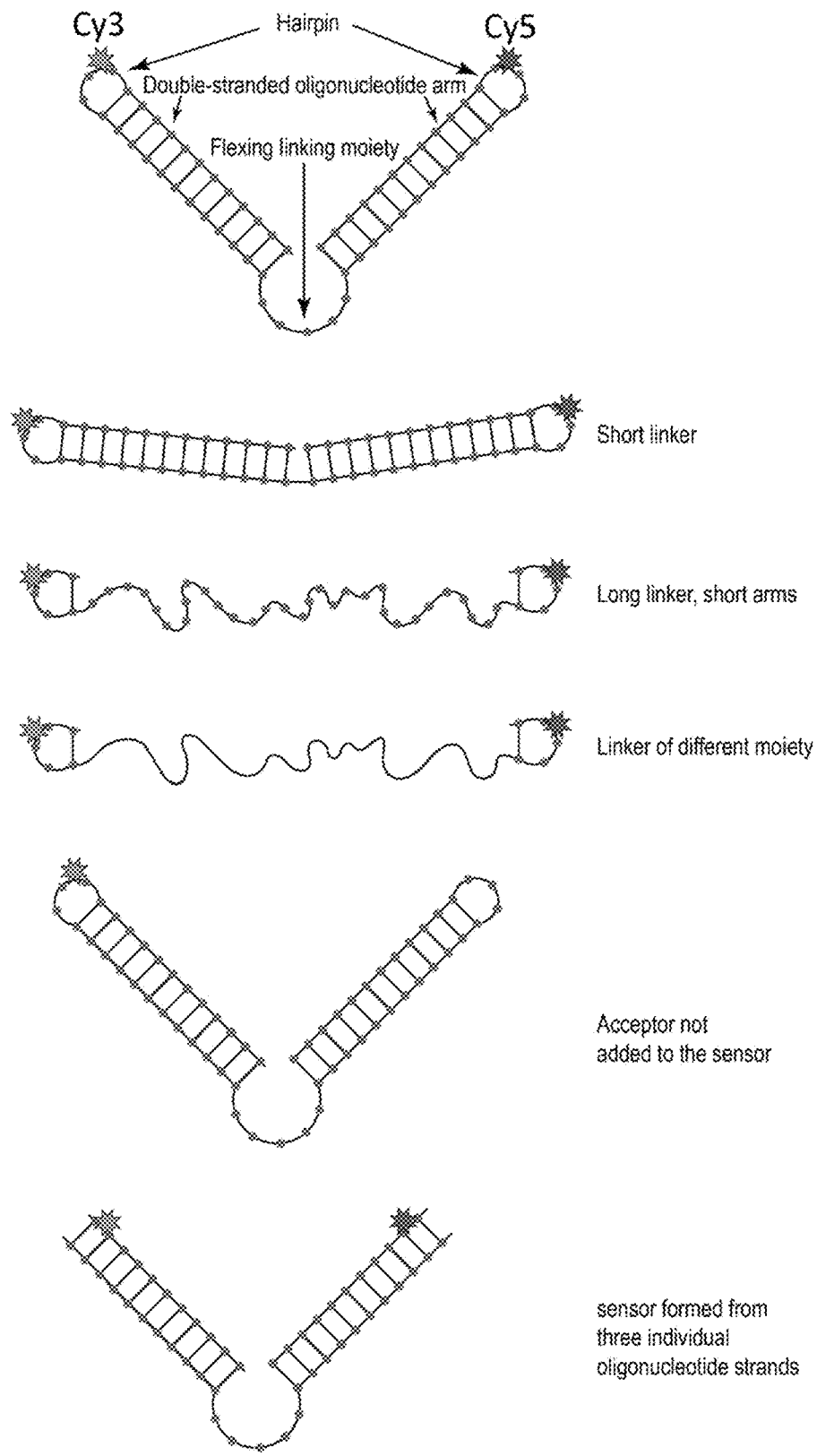
FIG. 1 shows a schematic diagram of one variant of the sensor showing the main elements, as well as examples of other variants.

Although claimed subject matter will be described in terms of certain examples, other examples, including examples that do not provide all of the benefits and features set forth herein, are also within the scope of this disclosure. Various structural, logical, and process step changes may be made without departing from the scope of the disclosure.

Ranges of values are disclosed herein. The ranges set out a lower limit value and an upper limit value. Unless otherwise stated, the ranges include all values to the magnitude of the smallest value (either lower limit value or upper limit value) and ranges between the values of the stated range.

As used herein, unless otherwise stated, the term "group" refers to a chemical entity that has one terminus that can be covalently bonded to other chemical species. Examples of groups include, but are not limited to:

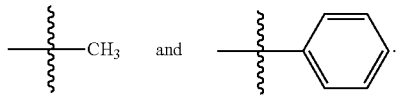

As used herein, unless otherwise stated, the term "moiety" refers to a chemical entity that has two or more termini that can be covalently bonded to other chemical species. Examples of moieties include, but are not limited to:

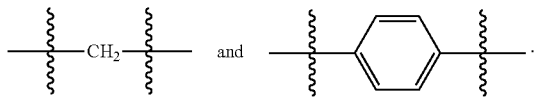

As used herein, unless otherwise indicated, the term "aliphatic" refers to branched or unbranched hydrocarbon groups that, optionally, contain one or more degrees of unsaturation. Degrees of unsaturation include, but are not limited to, alkenyl groups/moieties, alkynyl groups/moieties, and cyclic aliphatic groups/moieties. For example, the alphatic groups/moieties are a $C_1$ to $C_{40}$ aliphatic group/moiety, including all integer numbers of carbons and ranges of numbers of carbons therebetween (e.g., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, and $C_{40}$). The aliphatic group/moiety can be unsubstituted or substituted with one or more substituent. Examples of substituents include, but are not limited to, substituents such as, for example, halogens (—F, —Cl, —Br, and —I), aliphatic groups (e.g., alkyl groups, alkenyl groups, alkynyl groups, and the like), halogenated aliphatic groups (e.g., trifluoromethyl group), aryl groups, halogenated aryl groups, alkoxide groups, amine groups, nitro groups, carboxylate groups, carboxylic acids, ether groups, alcohol groups, alkyne groups (e.g., acetylenyl groups and the like), and the like, and combinations thereof.

As used herein, unless otherwise indicated, the term "aryl" refers to $C_5$ to $C_{30}$, including all integer numbers of carbons and ranges of numbers of carbons therebetween (e.g., $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, and $C_{30}$), aromatic or partially aromatic carbocyclic groups/moieties. An aryl group/moiety can also be referred to as an aromatic group/moiety. The aryl groups/moieties can comprise polyaryl moieties such as, for example, fused ring or biaryl moieties. The aryl group/moiety can be unsubstituted or substituted with one or more substituent. Examples of substituents include, but are not limited to, substituents such as, for example, halogens (—F, —Cl, —Br, and —I), aliphatic groups (e.g., alkenes, alkynes, and the like), aryl groups, alkoxides, carboxylates, carboxylic acids, ether groups, and the like, and combinations thereof. Examples of aryl groups/moieties include, but are not limited to, phenyl groups/moieties, biaryl groups/moieties (e.g., biphenyl groups/moieties and the like), and fused ring groups/moieties (e.g., naphthyl groups/moieties and the like).

The present disclosure provides molecular sensors and methods of using same. Molecular sensors of the present disclosure are oligonucleotide molecules (e.g., DNA, RNA, PNA, and the like) that bind substrates (e.g., small molecules, proteins, and the like). Molecular sensors of the present disclosure can be flexible molecular sensors or linear molecular sensors. The molecular sensors and methods of the present disclosure directly detect the binding (e.g., through intercalation, major groove binding, minor groove binding, electrostatic binding, and the like) of substrates to the oligonucleotides even if the substrate is not fluorescent, and further provide a quantitative measure of stoichiometry.

In an aspect, a molecular sensor of the present disclosure is a flexible molecular sensor.

A flexible molecular sensor of the present disclosure comprises a first double-stranded oligonucleotide (e.g., DNA, RNA, PNA, and the like, and combinations thereof, such as, for example, a DNA-RNA hybrid, more than two DNA strands hybridized using DNA origami methods as known in the art) arm, a second double-stranded oligonucleotide (e.g., DNA, RNA, PNA, and the like, and combinations thereof, such as, for example, a DNA-RNA hybrid, more than two DNA strands hybridized using DNA origami methods) arm, and a linking moiety (e.g., a flexible linking moiety). The linking moiety (e.g., a flexible linking moiety) connects (e.g., is covalently bonded to) the first double-stranded oligonucleotide arm at one strand of the first double-stranded arm and to the second double-stranded oligonucleotide arm at one strand of the second double-stranded arm. Each double-stranded oligonucleotide arm further comprises a fluorescent group (e.g., a group derived from a fluorescent molecule) that are attached (e.g., covalently bonded, non-covalently bound through, such as, for example, biotin-avidin binding) to each arm, such that the fluorescent groups or derivatives thereof may interact. In an example, the first double-stranded oligonucleotide arm has a first fluorescent group (e.g., a group derived from a fluorescent molecule, such as, for example, a donor chromophore or a group derived therefrom) and the second double-stranded oligonucleotide arm has a second fluorescent group (e.g., a group derived from a fluorescent molecule, such as, for example, an acceptor chromophore or a group derived therefrom), where the first fluorescent group or derivative thereof and the second fluorescent group or derivative thereof are positioned such that the first fluorescent group or derivative thereof and the second fluorescent group or derivative thereof can interact with each other (e.g., exhibit a change in Fluorescence Resonance Energy Transfer (FRET) efficiency as the first fluorescent group or derivative thereof and the second fluorescent group or derivative thereof are spatially separated).

The flexible linking moiety is flexible in a manner similar to the hinge of tongs, or a coiled string, such that it allows for movement of the double-stranded oligonucleotide arms. Flexible, as used when describing a linking moiety, refers to the ability of a flexible linking moiety to change its bending or coiling conformation in response to at least one change in an interaction between the sensor arms or at least one change in an interaction of the sensor with components in the medium in which the sensor is present. Non-limiting examples of flexible linking moieties include aliphatic moieties, aryl moieties, PEG moieties, single-stranded DNA oligonucleotide moieties, single-stranded RNA moieties, single-stranded PNA moieties, sugar phosphate moieties (i.e., a DNA backbone without the nucleobases), and peptide moieties. In various examples, the linking moiety does not base-pair with the oligonucleotide arms. In an example, a flexible linking moiety does not base-pair to any other region of the molecular sensor.

The linking moiety (e.g., a flexible linking moiety) can have various lengths. In various examples, the flexible linking moiety is 10 nm or less in length (e.g., 4 nm or less in length). In various examples, the flexible linking moiety is single-stranded DNA, single-stranded RNA, single-stranded PNA, or a combination thereof and is 50 bases or less in length. In various other examples, the flexible linking moiety is 40 bases or less in length. In various other examples, the flexible linking moiety is 30 bases or less in length. In various other examples, the flexible linking moiety is 20 bases or less in length. In various other examples, the same flexible linking moiety is 10 bases or less in length. In various other examples, the flexible linking moiety is a single atom long (e.g., a methylene moiety). In various examples, a flexible linking moiety is 100 nm in length (e.g., a PEG moiety that is 100 nm in length).

The double-stranded oligonucleotides arms are stiff (i.e., rigid) in solution, such that they are stiffer than the flexible linking moiety (i.e., the double-stranded oligonucleotide arms do not substantially bend) and such that the arms minimally change their conformation in the medium in which they are located. The stiffness of the double-stranded oligonucleotide arms is related to the bending rigidity of the double-stranded oligonucleotide. The double-stranded oligonucleotide arms have a persistence length, which is the length at which the double-stranded oligonucleotide arm retains stiffness (i.e., rigidity) in solution. In an example, length of the oligonucleotide arms may be determined based on the persistence length of the specific type of oligonucleotide used in solution (e.g., DNA has a persistence length of about 50 nm), such that a double-stranded oligonucleotide arm has a length similar to the persistence length of the oligonucleotide of choice or less (e.g., a double-stranded DNA oligonucleotide arm having a length of 50 nm±10 nm). In an example, a double-stranded DNA oligonucleotide arm is about 50 nm or less in length (e.g., 140-160 base pairs or less in length (e.g., 140-150 based pairs in length)). The double-stranded oligonucleotide arms may be the same length or substantially the same length. In various examples, the double stranded oligonucleotide arms are one base pair in length and have a hairpin (e.g., the double stranded oligonucleotide arm is about 0.5 nm long), such as in FIG. 1.

In an example, the oligonucleotide arms are thicker than standard double-stranded DNA. In such an example, the oligonucleotide arm can be prepared using DNA origami techniques known in the art.

In an example, the double-stranded oligonucleotide arms are substantially double-stranded (e.g., portions of the double-stranded oligonucleotide arm has at least one section that is double-stranded and at least one section that is single-stranded).

In various examples, the nucleobase sequence of the double-stranded oligonucleotide arms is random, or designed to confer binding specificity to a target of interest. For example, the double-stranded oligonucleotide arms can be designed to have adenine- and thymine-rich regions, or guanine- and cytosine-rich regions. In various examples, a specific oligonucleotide sequence is designed such that binding molecules bind (e.g., a molecule of interest, such as, for example, a drug) specifically to the sequence.

In an example, the flexible molecular sensor is a continuous sequence of DNA having a plurality of portions of complementarity within the sequence. The complimentary bases within such portions of complementarity of the DNA sequence hybridize such that a first double-stranded arm is formed having a hairpin structure and the strand continues to form the linking moiety (e.g., flexible linking moiety). The linking moiety (e.g., flexible linking moiety) continues into the next portion of complementarity such that the second double-stranded oligonucleotide arm, also having a hairpin structure therein, is formed. The first double-stranded arm has a first fluorescent group or derivative thereof (e.g., the first fluorescent group or derivative thereof is attached (e.g., covalently bonded) to the first double-stranded oligonucleotide arm in the hairpin structure) and the second double-stranded arm has a second fluorescent group or derivative thereof (e.g., the second fluorescent group or derivative thereof is attached (e.g., covalently bonded) to the second double-stranded oligonucleotide arm in the hairpin structure). A flexible molecular sensor having this structure is depicted in FIG. 1.

In an example, the flexible molecular sensor comprises two double-stranded oligonucleotide arms and a flexible linking moiety, where the flexible molecular sensor is not a continuous strand of DNA having a plurality of portions of complementarity. For example, the flexible molecular sensor is three sequences of DNA, where the first DNA sequence is longer than the second and third DNA sequences, the second DNA sequence is complimentary to a section of the first DNA sequence, such as, for example, a section of the first DNA sequence near its 3' end, and the third DNA sequence is complimentary to a section of the first DNA sequence, such as, for example, a section of the first DNA sequence near its 5' end.

The fluorescent groups or derivatives thereof exhibit a change in their fluorescence properties as a spatial separation occurs between the fluorescent groups or derivatives thereof (e.g., FRET, quenching, and the like). Non-limiting examples of fluorescence properties that change include intensity, absorption, emission, and the like. Examples of fluorescent groups or derivatives include Cy3 (e.g., a group derived from Cy3) and Cy5 (e.g., a group derived from Cy5), fluorescein (e.g., a group derived from fluorescein) and tetramethylrhodamine (e.g., a group derived from tetramethylrhodamine), 5-((2-acetamidoethyl)amino)naphthalene-1-sulfonic acid (e.g., a group derived from 5-((2- acetamidoethyl)amino)naphthalene-1-sulfonic acid) or 5-((2-Aminoethyl)amino)naphthalene-1-sulfonic acid (e.g., a group derived from 5-((2-Aminoethyl)amino)naphthalene-1-sulfonic acid) and fluorescein (e.g., a group derived from fluorescein), 5-((2-acetamidoethyl)amino)naphthalene-1-sulfonic acid (e.g., a group derived from 5-((2-acetamidoethyl)amino)naphthalene-1-sulfonic acid) or 5-((2-Aminoethyl)amino)naphthalene-1-sulfonic acid (e.g., a group derived from 5-((2-Aminoethyl)amino)naphthalene-1-sulfonic acid) and (E)-4-((4-(dimethylamino)phenyl)diazenyl) benzoic acid (e.g., a group derived from (E)-4-((4-(dimethylamino)phenyl)diazenyl)benzoic acid), fluorescein (e.g., a group derived from fluorescein) and fluorescein (e.g., a group derived from fluorescein), BODIPY (e.g., a group derived from BODIPY) and BODIPY (e.g., a group derived from BODIPY), fluorescein (e.g., a group derived from fluorescein) and QSY7 (e.g., a group derived from QSY7) and QSY9 (e.g., a group derived from QSY9), various combinations of Alexa Fluor dyes (e.g., Alexa 488—Alexa 555, and groups derived therefrom), various combinations of ATTO days (e.g., Atto 488—Atto 532, and groups derived therefrom), and the like. Other suitable groups are known in the art. In an example, the first fluorescent group or derivative thereof and/or second fluorescent group or derivative thereof replaces a nucleobase in the flexible molecular sensor. The first fluorescent group or derivative thereof and/or second fluorescent group or derivative thereof may be anywhere on the first double-stranded oligonucleotide arm and the second double-stranded oligonucleotide arm (e.g., the tip of the arm, the middle of the arm, or close to the flexible linking moiety), such that the first fluorescent group or derivative thereof and/or second fluorescent group or derivative thereof can interact with each other.

In an example, the flexible molecular sensor comprises two double-stranded DNA oligos (~12 base pairs), each labelled at only the hairpin structure with fluorescent groups or derivatives thereof (e.g., fluorophores) that form a FRET pair. A short sequence of single-stranded DNA connects the two oligos. Because the single-stranded DNA has degrees of freedom, it can rotate and "bend" in the middle, thus forming the shape of tongs or tweezers. The degree to which it bends changes the distance between the FRET pair and thus FRET efficiency. Binding of substrates can change the bending through binding of substrates that bind the DNA through groove-binding. The molecular sensor of the present disclosure may also be used in screens for drugs. Macromolecular crowding can also bring the double-stranded arms closer to each other, thus increasing FRET efficiency. The molecular sensor of the present disclosure may therefore be used to measure or compare macromolecular crowding.

In an aspect, the present disclosure provides linear molecular sensors.

Figure 15:
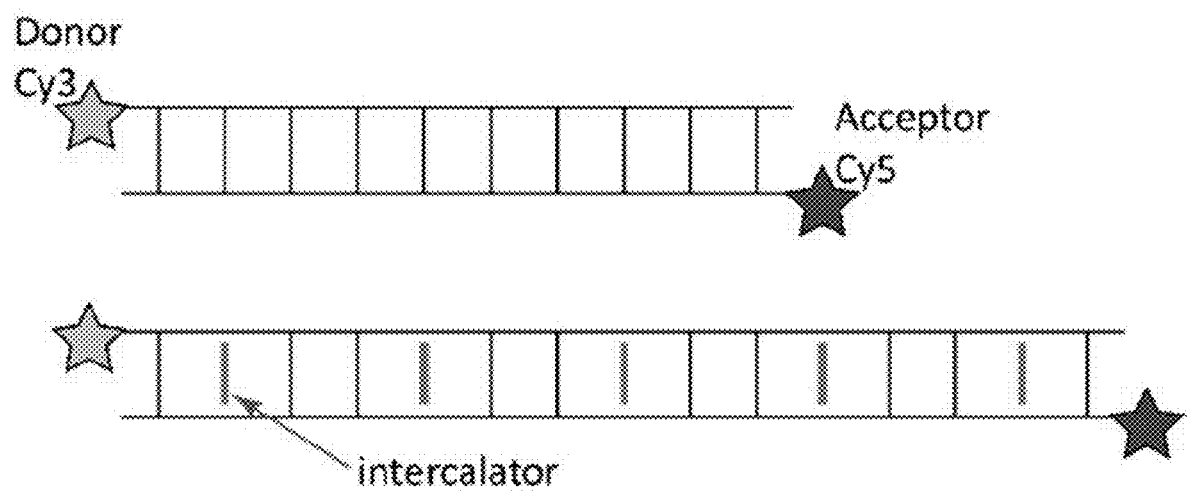
FIG. 15 shows a schematic of the dsDNA based intercalator sensor.
Figure 21:
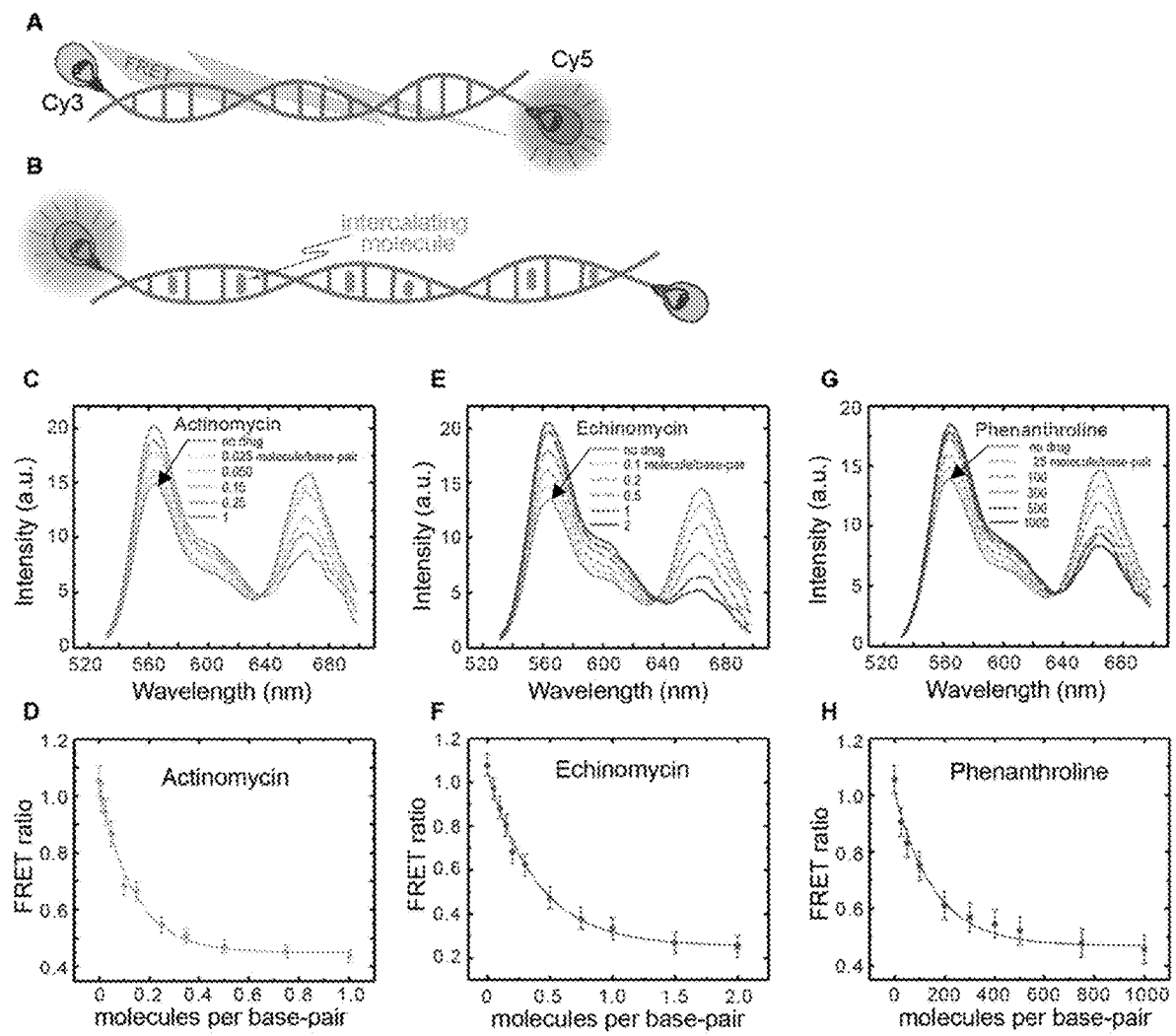
FIG. 21 shows an oligonucleotide probe of the present disclosure is sensitive to intercalating compounds in a concentration-dependent manner. A) The design of the double-stranded oligo probe, labelled with a FRET pair on opposite ends, allows for a change in FRET efficiency when intercalating molecules wedge between the DNA bases as shown in (B). Intercalation distorts the DNA resulting in an increase in the distance between the fluorophores and a drop in the FRET signal. (C) Fluorescence spectra of the probe excited at a wavelength of 500 nm show an increased donor fluorescence (570 nm) and decreased acceptor fluorescence (670 nm) as the concentration of the intercalating drug Actinomycin is increased. (D) The ratio of peak acceptor/peak donor fluorescence intensity (FRET ratio) is calculated to characterize the extent of energy transfer. The FRET ratio decreases with Actinomycin concentration indicating that the oligo probe extends in length when the drug wedges between its bases. A similar effect is seen with two other intercalating molecules, Echinomycin (E-F), and Phenanthroline (G-H). The concentration of the intercalator at saturation is different for different compounds and can therefore report on the binding constant as detailed in FIG. 22.

In an example, the linear molecular sensor of the present disclosure comprises a double-stranded oligonucleotide (e.g., DNA, RNA, PNA, and the like). Each 5' end is labelled with a fluorescent group or derivative thereof (e.g., a first fluorescent group or derivative thereof, such as, for example, a donor chromophore or derivative thereof and a second fluorescent group or derivative thereof, such as, for example, an acceptor chromophore or derivative thereof). Such a sensor is depicted in FIGS. 15 and 21.

In an example, the fluorescent groups or derivatives thereof exhibit a change in their fluorescence properties when a spatial separation occurs between the fluorescent groups or derivatives thereof changes (e.g., FRET, quenching, and the like). Non-limiting examples of fluorescence properties that change include intensity, absorption, emission, and the like). Examples of fluorescent groups or derivatives include Cy3 (e.g., a group derived from Cy3), Cy5 (e.g., a group derived from Cy5), fluorescein (e.g., a group derived from fluorescein) and tetramethylrhodamine (e.g., a group derived from tetramethylrhodamine), 5-((2-acetamidoethyl)amino)naphthalene-1-sulfonic acid (e.g., a group derived from 5-((2-acetamidoethyl)amino)naphthalene-1-sulfonic acid) or 5-((2-Aminoethyl)amino)naphthalene-1-sulfonic acid (e.g., a group derived from 5-((2-Aminoethyl)amino)naphthalene-1-sulfonic acid) and fluorescein (e.g., a group derived from fluorescein), 5-((2-acetamidoethyl)amino)naphthalene-1-sulfonic acid (e.g., a group derived from 5-((2-acetamidoethyl)amino)naphthalene-1-sulfonic acid) or 5-((2-Aminoethyl)amino)naphthalene-1-sulfonic acid (e.g., a group derived from 5-((2-Aminoethyl)amino)naphthalene-1-sulfonic acid) and (E)-4-((4-(dimethylamino)phenyl)diazenyl)benzoic acid (e.g., a group derived from (E)-4-((4-(dimethylamino)phenyl)diazenyl)benzoic acid), fluorescein (e.g., a group derived from fluorescein) and fluorescein (e.g., a group derived from fluorescein), BODIPY (e.g., a group derived from BODIPY) and BODIPY (e.g., a group derived from BODIPY), fluorescein (e.g., a group derived from fluorescein) and QSY7 (e.g., a group derived from QSY7) and QSY9 (e.g., a group derived from QSY9), various combinations of Alexa Fluor dyes (e.g., Alexa 488—Alexa 555, and groups derived therefrom), various combinations of ATTO days (e.g., Atto 488—Atto 532, and groups derived therefrom), and the like. In an example, the first fluorescent group or derivative thereof and/or second fluorescent group or derivative thereof replaces a nucleobase in the linear molecular sensor.

In an example, the linear molecular sensor is composed of a 15 base-pair double-stranded DNA that is labelled at both ends with fluorophores that form a FRET pair. This sensor can report on factors that can increase the distance between the fluorophores, such as, for example, drug molecules binding to the DNA through intercalation. By measuring changes in the FRET efficiency, the sensor can be used in drug screens for DNA-binding compounds.

Examples of intercalating substrates that bind to molecular sensors of the present disclosure include, but are not limited to, dactinomycin, amiloride hydrochloride, amodiaquine dihydrochloride, modaline sulfate, apomorphine hydrochloride, ethyl vanillin, benserazide hydrochloride, propranolol hydrochloride (+/−), gemifloxacin mesylate, tilorone, chloroquine diphosphate, acrisorcin, octocrylene, prazosin hydrochloride, primaquine phosphate, guanabenz acetate, quinacrine hydrochloride, quinidine gluconate, tacrine hydrochloride, aminacrine, progesterone, methoxsalen, hycanthone, naphazoline hydrochloride, sodium nitroprusside, carvedilol, symclosene, methysergide maleate, acepromazine maleate, perphenazine, acetophenazine maleate, alfuzosin hydrochloride, doxazosin mesylate, cisplatin, carvedilol phosphate, chloryrifos, oltipraz, guanidine hydrochoride, pyronaridine tetraphosphate, tropisetron hydrochloride, dequalinium chloride, berberine chloride, aloin, diacerin, khellin, chloramine-T, hydroquinidine, harmol hydrochloride, dictamnine, linamarin, palmatine chloride, cotarnine chloride, harmaline, lupeol acetate, N,N-hexamethyleneamiloride, haematoxylin pentaacetate, chrysin dimethyl ether, harmane, 2,2'-azo-bis-2-aminopropane, plumbagin, rhoifolin, harmine, 4'-methoxyflavone, rutilantinone, dactinomycin, chloroquine diphosphate, quinacrine hydrochloride, acriflavinium hydrochloride, coralyne chloride, echinomycin, and the like.

In an aspect, the present disclosure provides compositions comprising a molecular sensor of the present disclosure (e.g.

a linear molecular sensor and/or a flexible molecular sensor) and suitable buffers known in the art.

In an aspect, the present disclosure provides methods for using molecular sensors of the present disclosure (e.g., linear and/or flexible molecular sensors of the present disclosure). Methods of the present disclosure involve determining binding of at least one substrate (e.g., at least one small molecule, at least one protein, and the like, and combinations thereof). Additionally, methods of the present disclosure comprise determining molecular crowding.

Methods of the present disclosure may be high throughput methods. High throughput methods may be used to identify one or more substrates (e.g., at least one small molecule, at least one protein, and the like, and combinations thereof) that will bind to a molecular sensor of the present disclosure. Substrates that bind to molecule sensors may be intercalators, major groove binders, minor groove binders, substrates that covalently bind to the sensor, substrates that electrostatically bind to the sensor, or a combination thereof.

In an example, a method of the present disclosure for detecting binding of at least one substrate (e.g., at least one small molecule, at least one protein, and the like, and combinations thereof) comprises: i) contacting in a medium (e.g., an aqueous medium) the at least one substrate with a molecular sensor of the present disclosure (e.g., flexible molecular sensor or linear molecular sensor) or a composition of the present disclosure; ii) measuring a change (i.e., increase or decrease) in fluorescence of molecular sensor of the present disclosure or a composition of the present disclosure relative to a reference fluorescent value of the molecular sensor of the present disclosure or composition of the present disclosure in the absence of the substrate, where the change in fluorescence is indicative of binding of the substrate to the molecular sensor. Binding may be an intercalation binding event, a major groove binding event, a minor groove binding event, a covalent binding event, an electrostatic binding event, or a combination thereof.

Binding may be determined by the efficiency of energy transfer (e.g., such as observed in a FRET interaction). Efficiency of energy transfer can be used to determine distance between the interacting fluorescent groups.

The flexible molecular sensor can be used for detecting binding of a substrate (e.g., at least one small molecule, at least one protein, and the like, and combinations thereof). For example, a substrate can bind through major groove binding, minor groove binding, electrostatic binding, covalent binding, or a combination thereof. Binding of a substrate can cause a change in distance between the first double-stranded oligonucleotide arm and the second double-stranded oligonucleotide such that there is a spatial separation between the first fluorescent group or derivative thereof and the second fluorescent group or derivative thereof causing a change the interaction level (e.g., FRET efficiency) between the first fluorescent group or derivate thereof and the second fluorescent group or derivative thereof. Additionally, binding of a fluorescent substrate (i.e., a substrate having fluorescent properties) may be detected by a fluorescent substrate interacting with one of the fluorescent groups or derivatives thereof, such that there is a change in the fluorescent properties of the fluorescent group or derivative thereof.

The linear molecular sensor can be used for detecting binding of a substrate (e.g., at least one small molecule, at least one protein, and the like, and combinations thereof). For example, a substrate binds to the linear molecular sensor through intercalation, electrostatic binding, covalent binding, or a combination thereof. Binding of a substrate causes a change in length of the linear molecular sensor such that there is a spatial separation (e.g., binding of an intercalator causes an increase in length of the linear molecular sensor) between the first fluorescent group or derivative thereof and the second fluorescent group or derivative thereof, such that there is a change in the interaction (e.g., FRET efficiency) of the first fluorescent group or derivative thereof and second fluorescent group or derivative thereof. This is depicted in FIGS. 15 and 21.

In an example, a method of the present disclosure is performed on a test sample comprising an analyte of interest (e.g., a test sample containing a substrate, such as, for example, a small molecule drug, peptide, and/or the like).

In an example, a method is provided for the detection and measurement in solution and in living cells of dsDNA conformational changes that lead to changes in its length. Changes in length of the DNA occurs from binding of substrates. The method may be used to detect substrates binding to the DNA that alter the DNA double helix such as intercalating molecules, but is suitable for detecting any process that results in these changes. The method relies on modifying the DNA by adding two moieties that can exchange energy in a distance-dependent manner. Changes in the efficiency of this energy transfer is then correlated to changes in the DNA length. In an example, the efficiency of Fluorescence Resonance Energy Transfer (FRET) between a donor and an acceptor molecule attached to opposite ends of an oligonucleotide is used as a proxy for the length of the DNA. The molecular sensors of the present disclosure may be used to screen for and detect DNA-interacting drugs both in solution and in cells and to measure binding constants and stoichiometry. The use of such a construct to detect DNA-binding molecules that result in DNA structural changes is novel. The exact construct and labeling scheme is versatile and can be tuned for the specific application.

In an example, a method of the present disclosure can be performed in vivo and/or in vitro (e.g., cell culture).

In an example, a method of the present disclosure involves determining if a substrate has reached an organelle or cellular structure of interest. Such a method in cell culture comprises: i) transfecting the cells with a molecular sensor of the present disclosure; ii) imaging before and after introduction of a molecule of interest (e.g., a drug) that is being tested for oligonucleotide (e.g., DNA) binding within the cells. If the molecule of interest (e.g., a drug) penetrates the cell membrane, it will bind to the sensor, and the binding would be detected via a change in the fluorescence of the molecular sensor. Because the sensor is distributed throughout the cell, the molecule of interest (e.g., drug) reaching various cellular compartments (e.g., cell nucleus) in real time. Additionally, the amount of time taken for a particular molecule of interest (e.g., a drug) to reach particular compartment can be measured. Information on the uptake and distribution of a molecule of interest can be determined by imaging the sensor of the present disclosure within a cell as the sensor interacts with a molecule of interest (e.g., a drug). Molecules of interest may be referred to as substrates and/or compounds.

Concentration of a molecule of interest (e.g., a drug) is tuned based on the particular molecule of interest such that immediate saturation of the binding sites does not occur. Additionally, there may be biological reasons to tune the concentration of a molecule of interest (e.g., a drug).

The molecular sensors of the present disclosure may be used in conjunction with various imaging methods known in the art. For example, the molecular sensors of the present disclosure can be used in confocal microscopy methods that further include transfection methods.

A substrate may have a fluorescence excitation and/or emission that does not overlap with the excitation and/or emission of either the first fluorescent group or derivative thereof and/or second fluorescent group or derivative thereof on a molecular sensor of the present disclosure. Alternatively, the interaction of the at least one substrate with a molecular sensor of the present disclosure with the first fluorescent group or derivative thereof and/or second fluorescent group or derivative thereof may be used to detect binding of the at least one substrate to the molecular sensor of interest.

In an example, a method of the present disclosure is be used to measure molecular crowding (e.g., macromolecular crowding). Macromolecular crowding occurs when a large fraction of the volume of a solution is taken up by macromolecules. This has an effect of reducing the available volume in the solution which can result in, such as, for example the following: changes in the conformation of macromolecules (more compact structures would often be favored), altering the binding kinetics between molecules, and the like. For example, when using the flexible molecular sensor of the present disclosure, the more closed it is the more compact it is and therefore putting the sensor in a crowded solution favors a more closed conformation of the sensor. A closed conformation in turn brings the fluorophores closer to each other, therefore increasing the efficiency of energy transfer. Binding may not occur in a method to measure molecular crowding; however, weak binding may occurring depending on the molecular species involved.

In an example, a method for detecting molecular crowding comprises: i) contacting in a medium (e.g., an aqueous medium) the test sample with the molecular sensor of the present disclosure (e.g., a flexible molecular sensor or linear molecular sensor) or the composition of the present disclosure; ii) measuring a change (i.e., increase or decrease) in fluorescence of the molecular sensor or a composition relative to a reference fluorescence value of the molecular sensor or a composition in the absence of a substrate, where the change in fluorescence is indicative of the degree of molecular crowding.

In an aspect, the present disclosure provides methods of treating an individual in need of treatment comprising administering a compound to the individual in need of treatment, where the compound is an intercalator, major groove binder, minor groove binder, covalent binder, electrostatic binder, or the like, or a combination thereof.

Examples of intercalators include, but are not limited to, dactinomycin, amiloride hydrochloride, amodiaquine dihydrochloride, modaline sulfate, apomorphine hydrochloride, ethyl vanillin, benserazide hydrochloride, propranolol hydrochloride (+/−), gemifloxacin mesylate, tilorone, chloroquine diphosphate, acrisorcin, octocrylene, prazosin hydrochloride, primaquine phosphate, guanabenz acetate, quinacrine hydrochloride, quinidine gluconate, tacrine hydrochloride, aminacrine, progesterone, methoxsalen, hycanthone, naphazoline hydrochloride, sodium nitroprusside, carvedilol, symclosene, methysergide maleate, acepromazine maleate, perphenazine, acetophenazine maleate, alfuzosin hydrochloride, doxazosin mesylate, cisplatin, carvedilol phosphate, chloryrifos, oltipraz, guanidine hydrochoride, pyronaridine tetraphosphate, tropisetron hydrochloride, dequalinium chloride, berberine chloride, aloin, diacerin, khellin, chloramine-T, hydroquinidine, harmol hydrochloride, dictamnine, linamarin, palmatine chloride, cotarnine chloride, harmaline, lupeol acetate, N,N-hexamethyleneamiloride, haematoxylin pentaacetate, chrysin dimethyl ether, harmane, 2,2'-azo-bis-2-aminopropane, plumbagin, rhoifolin, harmine, 4'-methoxyflavone, rutilantinone, dactinomycin, chloroquine diphosphate, quinacrine hydrochloride, acriflavinium hydrochloride, coralyne chloride, and echinomycin. These compounds may be used to treat a condition where a method of treating the condition comprises administering a therapeutically effective amount of an intercalator alone or in combination with other compounds. For example, an intercalator may be used as an antineoplastic and/or as an antimicrobial or to treat conditions including, but not limited to, cancer and bacterial infections.

Examples of groove binders include, but are not limited to, Netropsin, Petamidine, Berenil, Mithramycin A/Plicamycin, Chromomycin A3, Duocarmycin, Anthramycin, Neocarzinostain, Esperamicin, Distamycin A. These compounds may be used to treat a condition where a method of treating the condition comprises administering a therapeutically effective amount of a groove binder alone or in combination with other compounds. For example, a groove binder may be used to treat conditions including, but not limited to, cancer and bacterial infections. A groove binder (e.g., minor groove binder) may be used as an antineoplastic and/or as an antimicrobial, antiviral, or RNA synthesis inhibitor.

In various examples, administering a compound further comprises identifying the compound as an intercalator, major groove binder, minor groove binder, covalent binder, electrostatic binder, or the like, or a combination thereof.

In an aspect, the present disclosure provides methods of identifying substrates (e.g., compounds) having a particular mode of binding (e.g., intercalation, major groove, minor groove, covalent, electrostatic, and the like, and combinations thereof). The substrates (e.g., compounds) having a particular mode of binding may then be used for treatment of conditions where other therapeutic agents exhibiting the same mode of binding are known to be useful. For example, a substrate identified as an intercalator by a method of the present disclosure utilizing a linear molecular sensor of the present disclosure may be suitable to treat a condition where other known therapies comprise administering intercalating compounds. Identification may be carried via a high throughput method, such as, for example, using a fluorescence plate reader and a multiwell plate (e.g., a 96-well plate, a 384-well plate, and the like).

In various examples, a method of treating with a compound (e.g., an identified compound) having a particular mode of binding comprises a) identifying the particular mode of binding of a compound (e.g., a substrate) by i) contacting in a medium (e.g., an aqueous medium) the at least one substrate with a molecular sensor of the present disclosure (e.g., flexible molecular sensor or linear molecular sensor) or a composition of the present disclosure; ii) measuring a change (i.e., increase or decrease) in fluorescence of molecular sensor of the present disclosure or a composition of the present disclosure relative to a reference fluorescent value of the molecular sensor of the present disclosure or composition of the present disclosure in the absence of the substrate, where the change in fluorescence is indicative of binding of the substrate to the molecular sensor, where the mode of binding may be determined based on the type of molecular sensor used (e.g., flexible molecular sensor or linear molecular sensor); b) administering a therapeutically effective amount of the identified compound to an individual in need of treatment having a condition where other therapeutic agents exhibiting the same mode of binding are known to be useful. For example, the method may be used to identify compounds that are intercalators using a linear molecular sensor of the present disclosure. The identified intercalating compound may be then used to treat conditions where intercalators are known to be useful for treatment of that condition.

Molecular sensors, substrates, compounds, and/or compounds identified by a method of the present disclosure (e.g., substrates identified by a method of the present disclosure) may be administered as a composition. The compositions described herein may include one or more standard pharmaceutically acceptable carriers. Pharmaceutically acceptable carriers may be determined in part by the particular composition being administered, as well as by the particular method used to administer the composition. Accordingly, there are a wide variety of suitable formulations of pharmaceutical compositions of the present disclosure. The compounds may be freely suspended in a pharmaceutically acceptable carrier. Examples of carriers include solutions, suspensions, emulsions, solid compositions that are dissolved or suspended in a solvent before use, and the like. The compositions may be prepared by dissolving, suspending or emulsifying one or more of the active ingredients in a diluent. Examples of diluents, include, but are not limited to distilled water for injection, physiological saline, vegetable oil, alcohol, dimethyl sulfoxide, and a combination thereof. Further, the compositions may contain stabilizers, solubilizers, suspending agents, emulsifiers, soothing agents, buffers, preservatives, and the like. The compositions may be sterilized in the final formulation step or prepared by sterile procedure. The composition of the disclosure may also be formulated into a sterile solid preparation, for example, by freeze-drying, and can be used after sterilized or dissolved in sterile water or other sterile diluent(s) immediately before use. Additional examples of pharmaceutically acceptable carriers include, but are not limited to, sugars, such as lactose, glucose, and sucrose; starches, such as corn starch and potato starch; cellulose, including sodium carboxymethyl cellulose, ethyl cellulose, and cellulose acetate; powdered tragacanth; malt; gelatin; talc; excipients, such as cocoa butter and suppository waxes; oils, such as peanut oil, cottonseed oil, safflower oil, sesame oil, olive oil, corn oil, and soybean oil; glycols, such as propylene glycol; polyols, such as glycerin, sorbitol, mannitol, and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. Additional non-limiting examples of pharmaceutically acceptable carriers can be found in: Remington: The Science and Practice of Pharmacy (2005) 21st Edition, Philadelphia, Pa. Lippincott Williams & Wilkins. Effective formulations include, but are not limited to, oral and nasal formulations, formulations for parenteral administration, and compositions formulated for with extended release. Parenteral administration includes infusions such as, for example, intramuscular, intravenous, intraarterial, intraperitoneal, subcutaneous administration, and the like.

Compositions comprising compounds, the compounds identified by a method described herein, substrates, and/or molecular sensors may be administered to an individual using any known method and route, including oral, parenteral, subcutaneous, intraperitoneal, intrapulmonary, intranasal, and intracranial injections. Parenteral infusions include, but are not limited to, intramuscular, intravenous, intraarterial, intraperitoneal, subcutaneous administration, and the like. Administration may also include, but is not limited to, topical and/or transdermal administrations.

The dose of the composition comprising a compound or compound identified by a method of the present disclosure and a pharmaceutical agent or comprising a molecular sensor may necessarily be dependent upon the needs of the individual to whom the composition of the disclosure is to be administered. These factors include, for example, the weight, age, sex, medical history, and nature and stage of the disease for which a therapeutic or prophylactic effect is desired. The compositions may be used in conjunction with any other conventional treatment modality designed to improve the disorder for which a desired therapeutic or prophylactic effect is intended, non-limiting examples of which include, but are not limited to, surgical interventions and radiation therapies. For example, the compositions are used in combination with (e.g., co-administered with) one or more known drugs.

Examples of composition forms include, but are not limited to, (a) liquid solutions, such as, for example, an effective amount of a compound of the present disclosure suspended in diluents, such as, for example, water, saline or PEG 400; (b) capsules, sachets, depots or tablets, each containing a predetermined amount of the active ingredient, as liquids, solids, granules or gelatin; (c) suspensions in an appropriate liquid; (d) suitable emulsions; and (e) patches. The liquid solutions described above may be sterile solutions. The compositions may comprise, for example, one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers.

A composition may be in unit dosage form. In such form, the composition may be subdivided into unit doses containing appropriate quantities of the active component. The unit dosage form may be a packaged preparation, the package containing discrete quantities of preparation, such as, for example, packeted tablets, capsules, and powders in vials or ampoules. Also, the unit dosage form may be a capsule, tablet, cachet, or lozenge itself, or it may be the appropriate number of any of these in packaged form. The composition can, if desired, also contain other compatible therapeutic agents. The compositions may deliver the compounds of the disclosure in a sustained release formulation.

Methods of the present disclosure may be used on various individuals. In various examples, an individual is a human or non-human mammal. Examples of non-human mammals include, but are not limited to, farm animals, such as, for example, cows, hogs, sheep, and the like, as well as pet, service, or sport animals such as, for example, horses, dogs, cats, and the like. Additional non-limiting examples of individuals include, but are not limited to, rabbits, rats, mice, and the like. The compounds or compositions of the present disclosure may be administered to individuals for example, in pharmaceutically-acceptable carriers, which facilitate transporting the compounds from one organ or portion of the body to another organ or portion of the body.

The steps of the method described in the various embodiments and examples disclosed herein are sufficient to carry out the methods of the present invention. Thus, in an embodiment, the method consists essentially of a combination of the steps of the methods disclosed herein. In another embodiment, the method consists of such steps.

The following examples are presented to illustrate the present disclosure. They are not intended to limiting in any matter.

EXAMPLE 1

This example provides a description of using molecular sensors of the present disclosure.

The molecular sensors of the present disclosure of this example are designed to report using Fluorescence Resonance Energy Transfer (FRET) on the binding of DNA intercalators or groove binders, both in living cells and in purified in vitro settings. The steps associated with the use of the sensors for this purpose are outlined below first in vitro and then in living cells in culture:

The molecular sensors were used in vitro according to the following: 1) The sensors were diluted in a NaCl solution (e.g., in a 50-100 mM NaCl solution) and 0.2% BSA solution to a concentration of 1 µM. This can be adjusted depending on the sensitivity of the fluorescence measurement device. 2) The fluorescence spectrum was measured using a fluorescence spectrophotometer, a plate reader, or any other ad-hoc means. This should be done by exciting the donor at a wavelength of light that does not fall within the acceptor excitation spectrum (500 nm for the Cy3-Cy5 pair used). 3) The molecular species was added to be characterized for DNA binding properties or to be tested for intercalating or groove binding ability. The appropriate sensor is used (e.g., a linear or flexible molecular sensor). The fluorescence spectrum was measured again using the same methods and settings. 4) The FRET ratio was compared for both the sensor alone and sensor plus tested molecule. The FRET ratio is calculated by dividing the peak intensity of the acceptor fluorescence by that of the donor fluorescence. For the intercalation sensor, a decrease in the FRET ratio indicates that the tested molecule binds the DNA. This is because intercalators wedge between the bases thus lengthening the sensor and increasing the donor-acceptor distance. For the groove-binding sensor, an increase in the FRET ratio indicates that the tested molecule binds the DNA. This is because groove-binders will screen the negative charge on the DNA, and therefore reduce the repulsion between the two double-stranded arms of the sensor, reducing the donor-acceptor distance.

The concentration of the tested molecules should be titrated for best sensitivity depending on the method used to measure fluorescence. The procedure outlined above can be automated using high throughput instrumentation for screens tailored for the identification of DNA-binding molecules.

EXAMPLE 2

This example provides a description of using molecular sensors of the present disclosure.

The molecular sensors were used in cell culture according to the following: 1) the desired cells were prepared in glass-bottom culture dishes or wells to a confluence lower than 70%. 2) Two hours before imaging, a desired transfection protocol (e.g., liposome transfection), and the like) is used with either sensor depending on the desired mode of DNA binding to be investigated. 3) After the transfection period, the culture was washed from excess sensors. 4) The culture disk was transferred to the confocal microscope for imaging. 5) The microscope was set for excitation of the donor at a wavelength of light that does not fall within the acceptor excitation spectrum (500 nm for the Cy3-Cy5 pair used). 6) If using filter cubes use the appropriate cubes to image donor fluorescence in one channel and acceptor fluorescence in the other. If using spectral imaging set the imaging wavelength windows for the two fluorophores. 7) Cells were identified that have been successfully transfected as indicated by fluorescence throughout the cell. 8) Images were acquired in both channels. 9) Software to calculate the ratio of acceptor/donor fluorescence (the FRET ratio) for the desired regions within the imaged cells was used. 10) The desired drug to be tested was added. 11) The cells were imaged again and the FRET ratio was calculated as a function of the desired variable: e.g. time, drug concentration, region within the cell, etc. A change in the FRET ratio indicates DNA drug binding.

This method can also be adapted for high throughput screens using high content technologies that allow the imaging of cells in 96 well-plate format.

EXAMPLE 3

This example provides a description of using flexible molecular sensors of the present disclosure.

The two double-stranded DNA arms are linked by a single-stranded DNA linker that renders the sensor flexible in the middle allowing it to bend (FIG. 1). Any factor that causes a change in the average bending of the sensor will also change the distance between the fluorophores labelling the sensor at the tips of the double-stranded arms. The fluorophores (Cy3 and Cy5) are chosen to interact via fluorescence resonance energy transfer (FRET), and therefore the efficiency of FRET relates to the distance between the fluorophores and can be used as a readout of the sensor bending.

Figure 2:
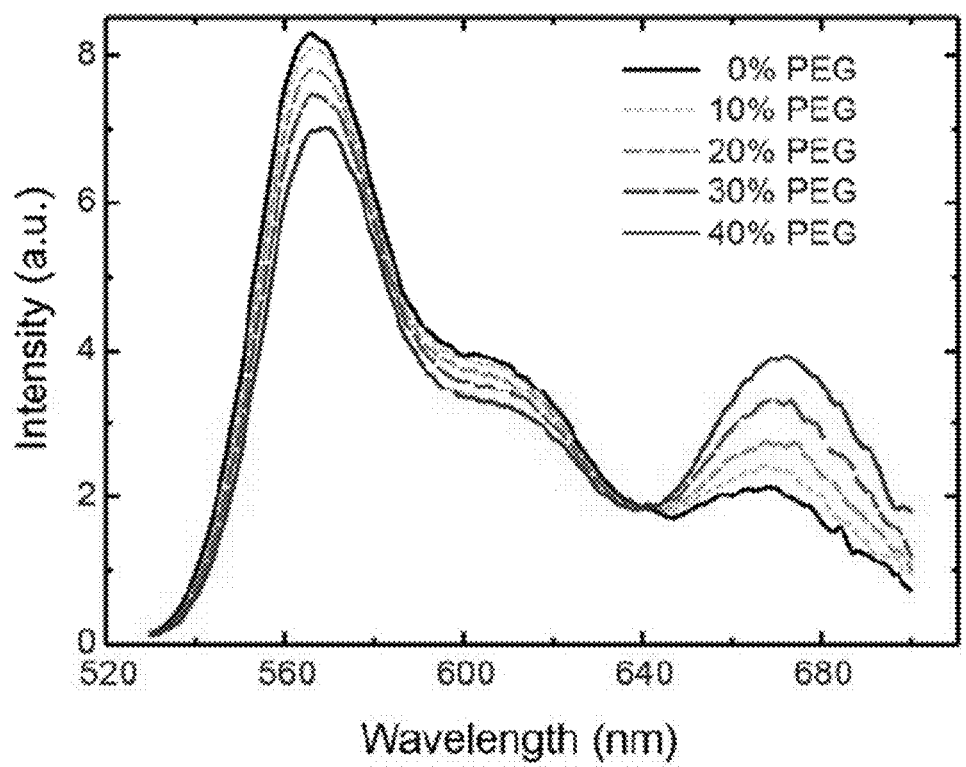
FIG. 2 shows spectra showing the change in the relative fluorescence of the donor and acceptor on the sensor as a function of increasing concentration of the crowding agent PEG.

The flexible sensor of the present disclosure was used in a method to collect spectra showing the change in the relative fluorescence of the donor and acceptor on the sensor as a function of increasing concentration of the crowding agent PEG (FIG. 2). Incubating the sensor in a solution of increasing concentration (w/w) of polyethylene glycol (PEG 6 kDa) increases the excluded volume in the solution therefore forcing the sensor to take a more closed conformation and increasing the efficiency of energy transfer. This is observed as an increase in the fluorescence of Cy5 (at 670 nm) and a concomitant decrease in the fluorescence of Cy3 (at 570 nm). These spectra were measured on a plate reader by exciting the donor (Cy3) at 500 nm and recording the spectra.

Figure 3:
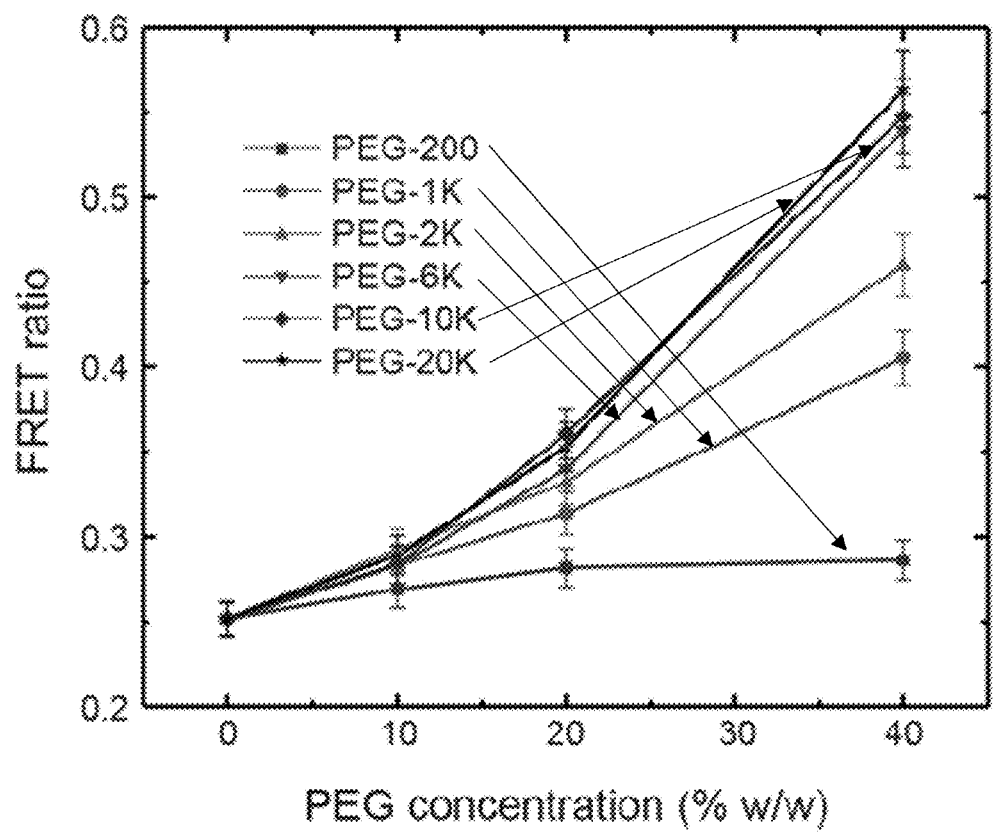
FIG. 3 shows FRET efficiency as a function of crowder concentration for PEG of various molecular weights.

FRET efficiency as a function of crowder concentration for PEG of various molecular weights was determined with the flexible sensor of the present disclosure (FIG. 3). A proxy to the efficiency of FRET is the FRET ratio which is the ratio of intensity at the peak of acceptor fluorescence to that at the peak of the donor fluorescence. The closer the sensor arms are to each other the larger the FRET ratio. Increasing the concentration of the crowder PEG increases the FRET ratio for all molecular weights, with the effect being small for the smallest molecular weight.

Figure 4:
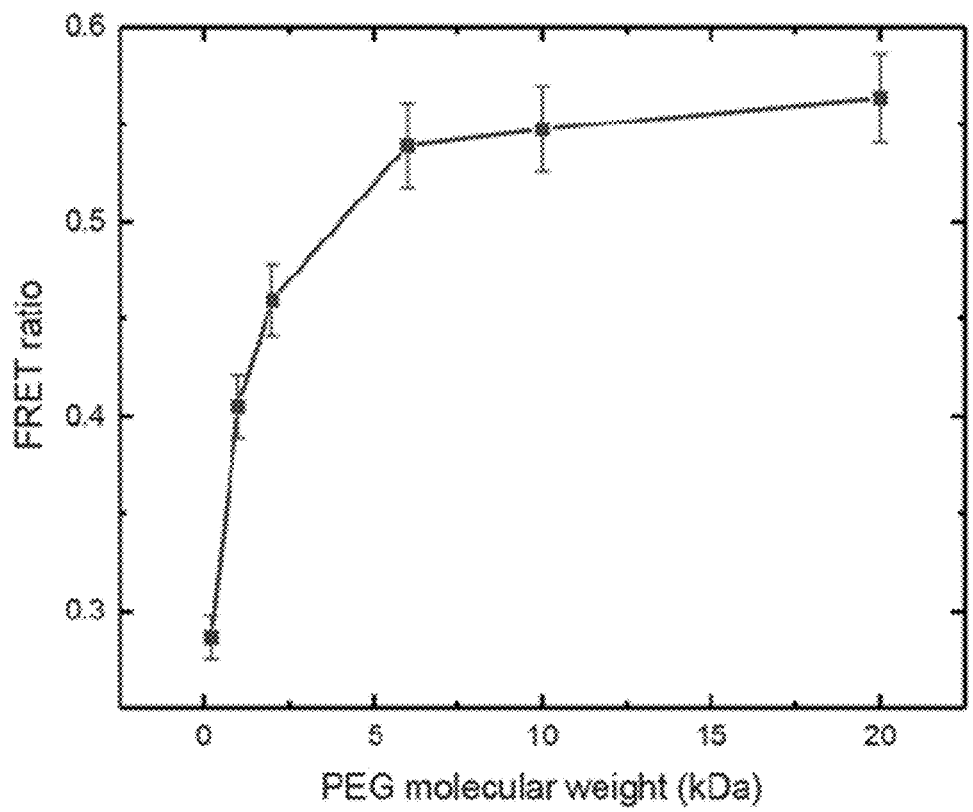
FIG. 4 shows FRET ratio increases with the PEG molecular weight.

The FRET ratio increases with the PEG molecular weight (FIG. 4). At 40% (w/w) of PEG, the larger the PEG molecule, the larger the FRET ratio. Starting with PEG of molecular weight of 6 kDa, the FRET ratio changes minimally with the size of the crowding molecule.

Figure 5:
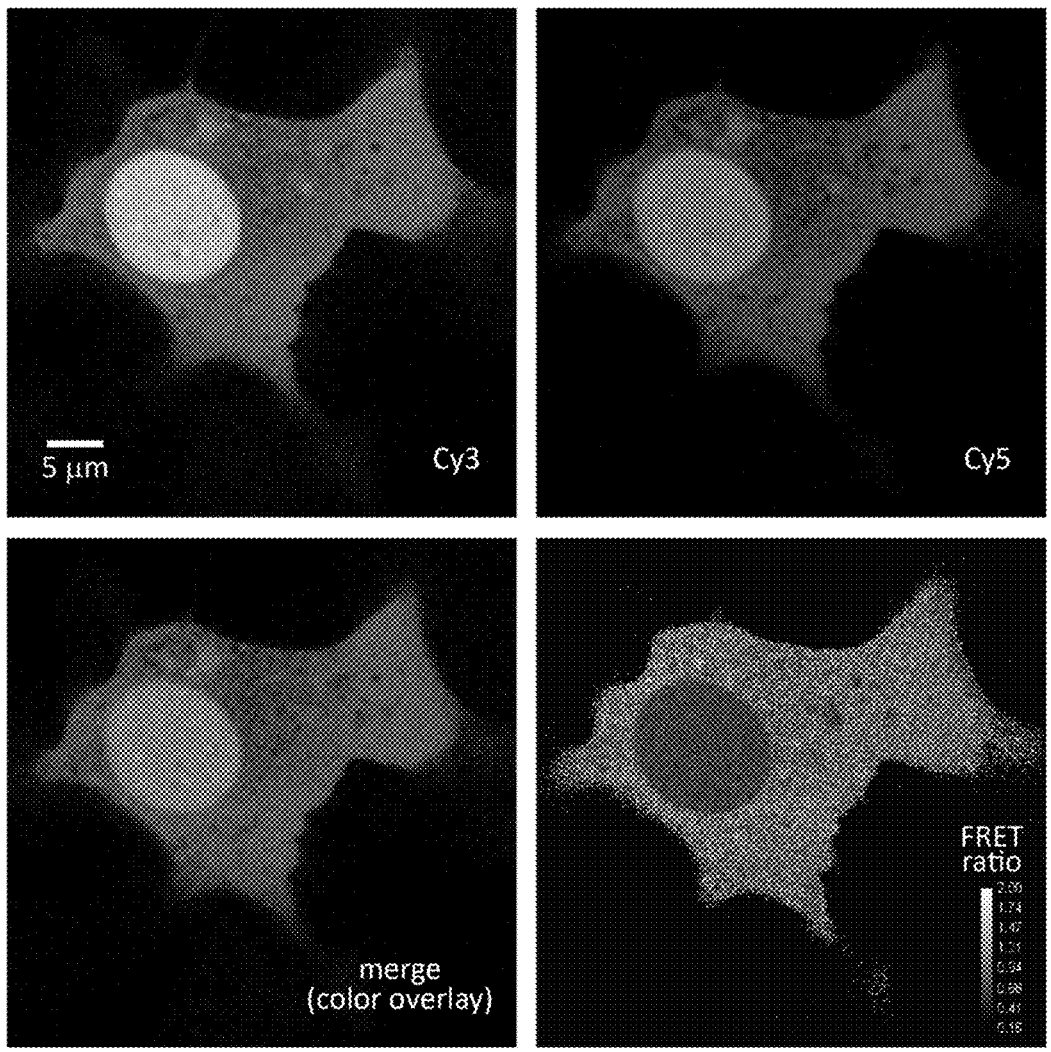
FIG. 5 shows a sensor of the present disclosure reports on the local macromolecular crowding within living cells in culture.

The flexible molecular sensors reports on the local macromolecular crowding within living cells in culture (FIG. 5). The sensor was introduced into cells by liposome transfection. After a short incubation period of 45 minutes, the cells plated on an imaging well were washed and imaged using scanning laser confocal microscopy. The cells were then imaged by exciting the donor (Cy3) and imaging the fluorescence of Cy3 and Cy5 (acceptor) in the appropriate spectral ranges (top two images). The false-colored images can be merged therefore producing another false color image where green (FIG. 5—top left) indicates a small FRET ratio and red (FIG. 5—top right) a large FRET ratio an intermediate values being yellow/orange (FIG. 5—bottom left). A quantitative measurement of the FRET ratio is represented as a gray scale image (FIG. 5—bottom right) where each pixel is in the ratio of the intensity in the Cy5 channel divided by that in the Cy3 channel. Local variations indicate local differences in the degree of macromolecular crowding. Most notably, the nucleus shows a distinctly lower FRET ratio than the cytosol.

Figure 6:
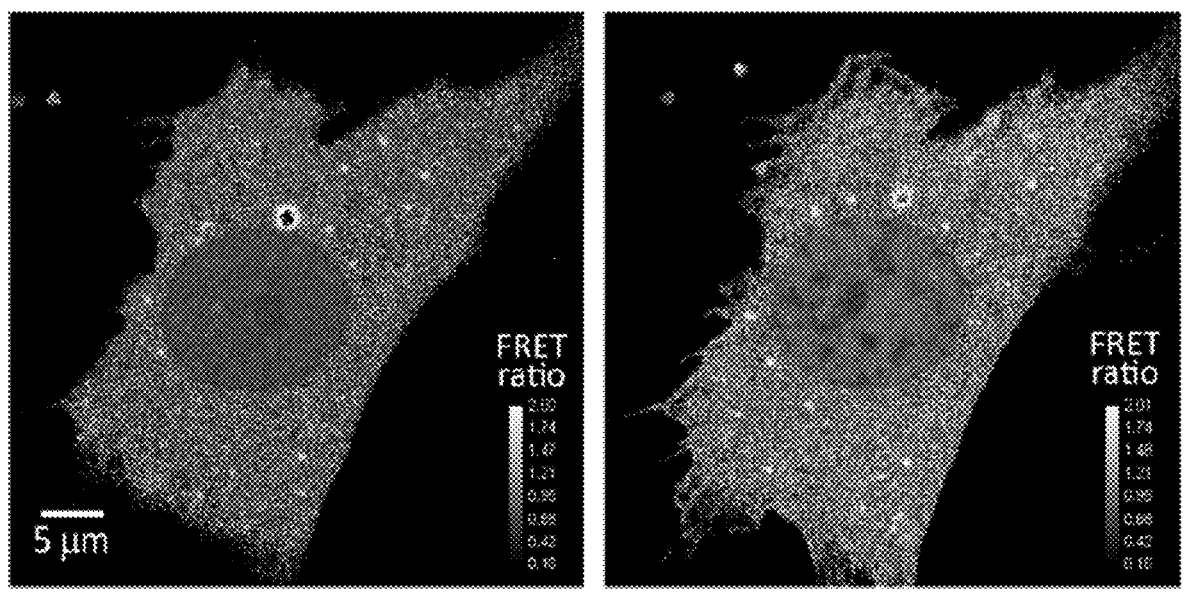
FIG. 6 shows increasing osmolarity of the medium shrinks the cells, thus increasing macromolecular crowding.

Increasing osmolarity of the medium shrinks the cells therefore increasing macromolecular crowding. (FIG. 6). The FRET ratio within a cell in normal culture medium is shown on the left. The sensor internalized within the cell remained sensitive to changes in macromolecular crowding as demonstrated by increasing the osmolarity of the medium using 750 mM NaCl which induced an efflux of water increasing the concentration of macromolecules and therefore increasing the FRET ratio (brighter image on the right).

Figure 7:
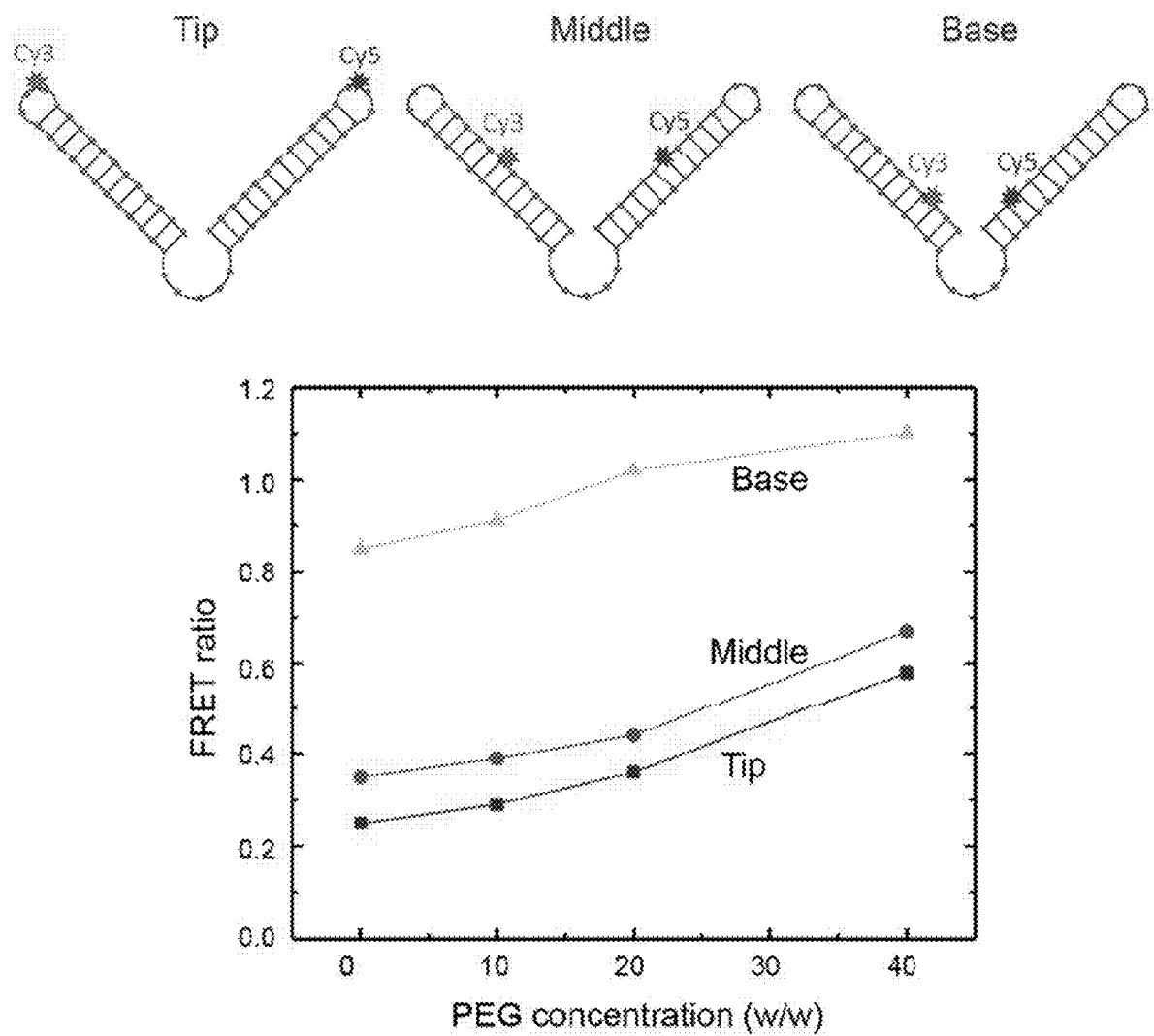
FIG. 7 shows sensor sensitivity can be tuned by changing the position of the FRET pair.

The flexible molecular sensor sensitivity can be tuned by changing the position of the FRET pair (FIG. 7). The efficiency of the FRET changes with distance and works over a range of a few nanometers (depending on the choice of the FRET pair). Therefore, the sensitivity of the sensor can be tuned to the desired range by placing the FRET pair anywhere along the double-stranded arms. Shown in the schematic at the top are three such positions (tip, middle, base) along the arms. The sensor with the FRET pair at the tip shows the largest sensitivity to changes in crowding in solution even though the FRET ratio is larger when the FRET pair is at the base since the fluorophores are close to each other.

Figure 8:
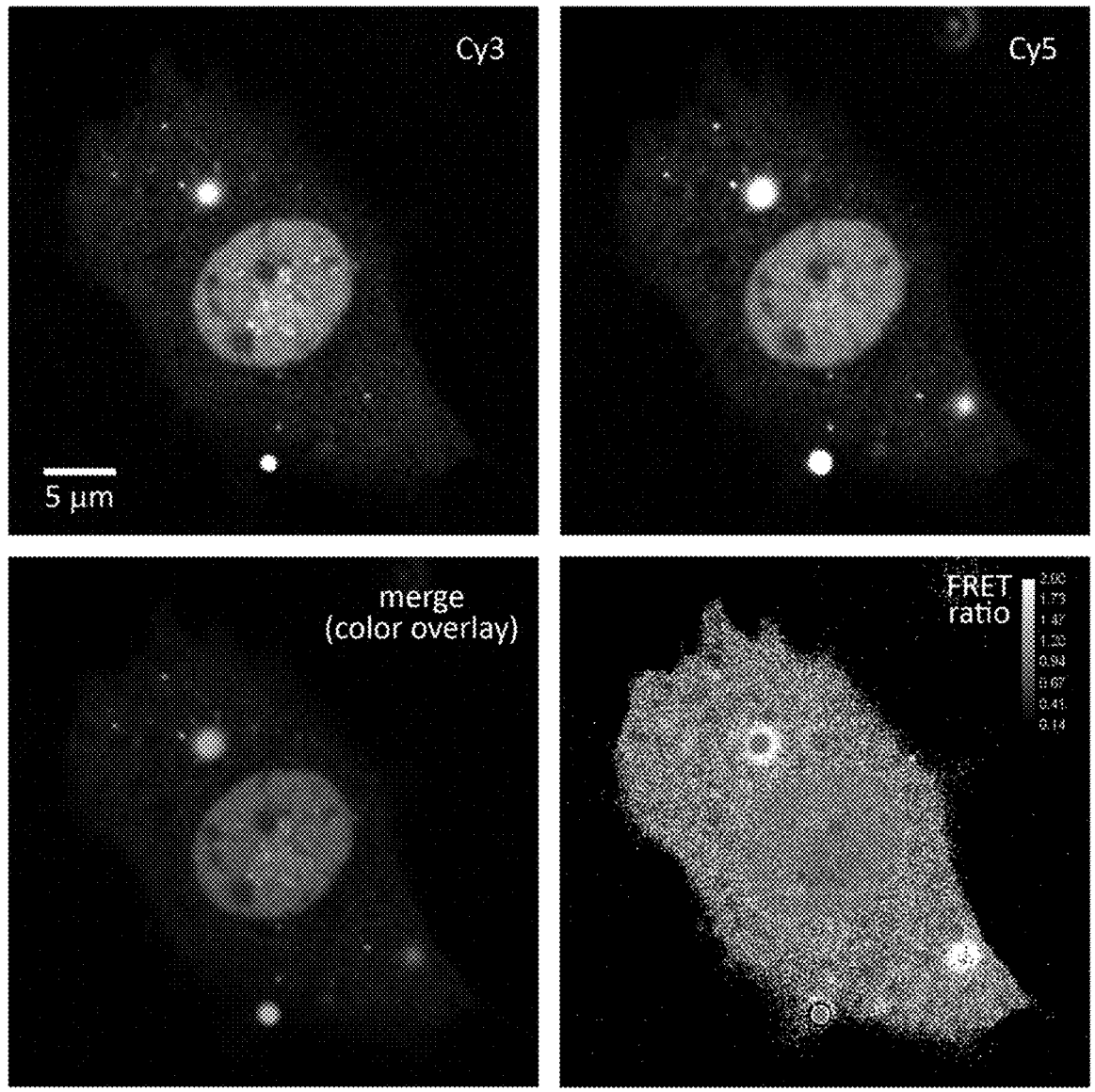
FIG. 8 shows a sensor with a FRET pair placed at the base of the double-stranded arms shows less contrast between the nucleus and the cytosol.

The flexible molecular sensor with the FRET pair placed at the base of the double-stranded arms shows less contrast between the nucleus and the cytosol (FIG. 8). With the FRET pair at the base, large changes in the distance between the arms barely change the distance between the FRET pair, thus reducing the contrast between the cytosol and the nucleus. However, the dynamic range of this variant of the sensor highlights small changes in crowding within the nucleus as shown in the FRET ratio image at the bottom right (compare to the homogeneous FRET ratio in the nucleus of FIG. 5 were the FRET pair was placed at the tip of the sensor arms).

Figure 9:
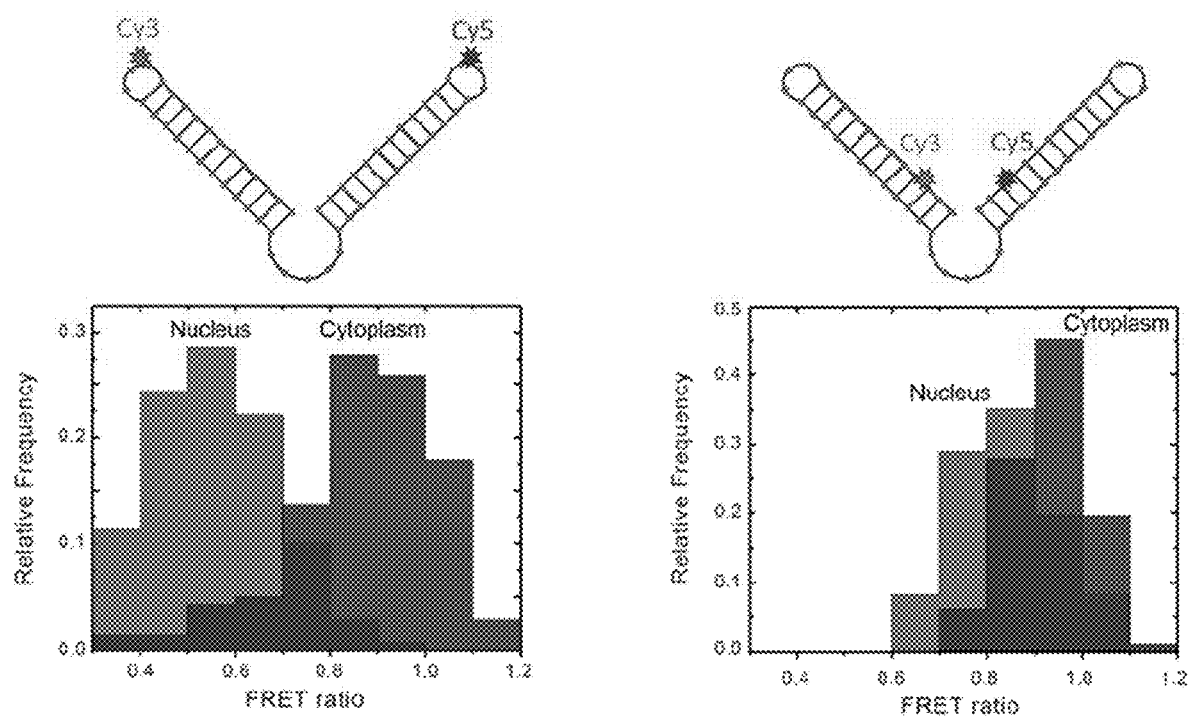
FIG. 9 shows the nucleus is less crowded than the cytoplasm.

The nucleus is less crowded than the cytoplasm (FIG. 9). The FRET efficiency measured in the nucleus and cytoplasm of around 100 cells shows a clear difference. The nucleus (green) is consistently less crowded than the cytoplasm (red). With the sensor having the FRET pair at the base of the arms (right), the difference between the nucleus and the cytoplasm is smaller than for the sensor with the FRET pair at the tip, as expected for a smaller dynamic range.

Figure 10:
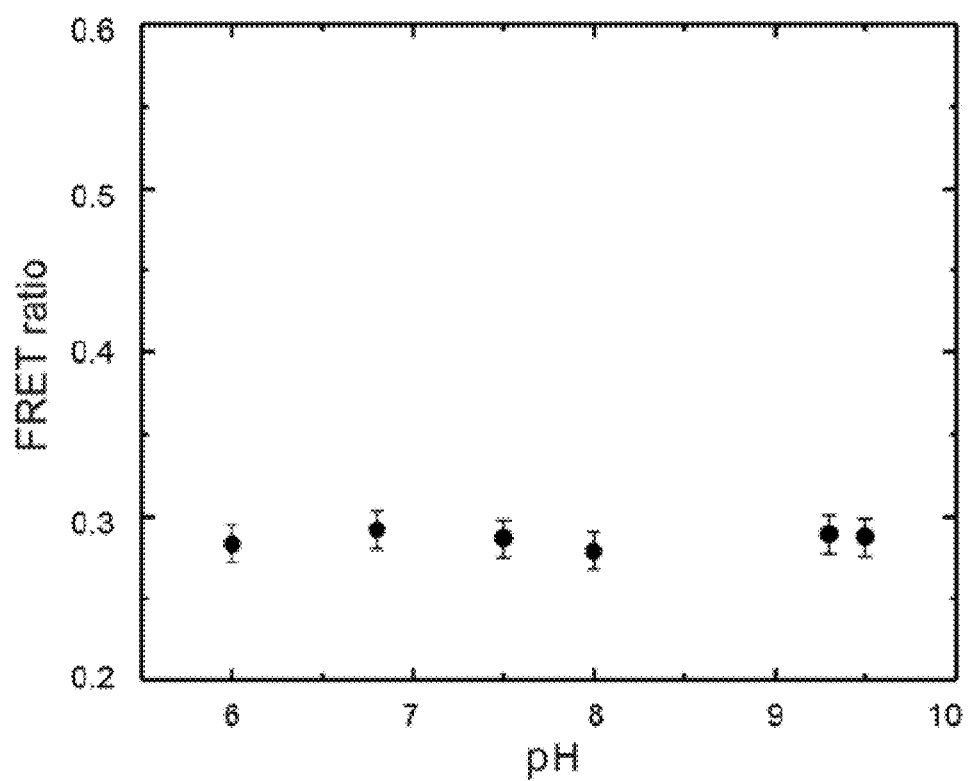
FIG. 10 shows a sensor of the present disclosure is insensitive to changes in pH.

The sensor is insensitive to changes in pH (FIG. 10). This rules out the possibility that changes in pH between the nucleus and cytosol are behind the difference in FRET ratio we observe.

Figure 11:
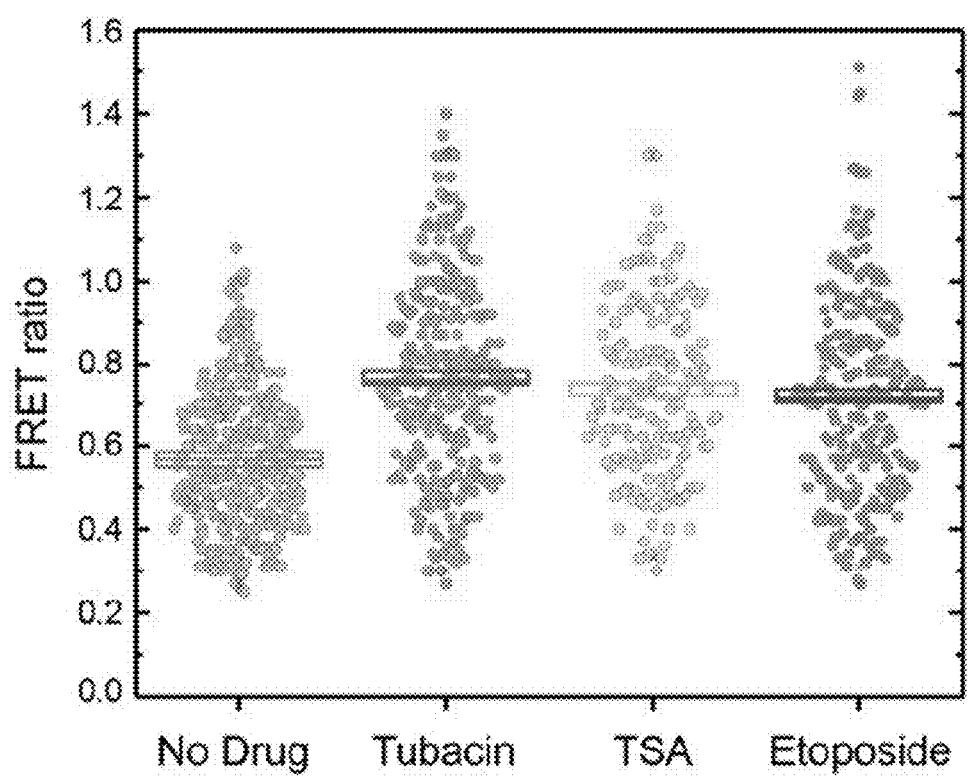
FIG. 11 shows drugs that disrupt chromatin compaction result in a more crowded nucleus.

Drugs that disrupt chromatin compaction result in a more crowded nucleus (FIG. 11). The FRET ratio was measured within the nuclei of cells in culture medium in the absence and presence of drugs that disrupt chromatin structure. Three drugs that disrupt chromatin in different ways were used: trichostatin A (TSA) and tubacin both of which inhibit histone deacetylases, and etoposide which forms a complex with DNA and topisomerase II resulting in the accumulation of DNA breaks. In all three cases, the resulting chromatin should be less compact and that is indeed reflected by the larger FRET ratio measured in the nuclei of cells treated with any of these drugs when compared to untreated cells.

Figure 12:
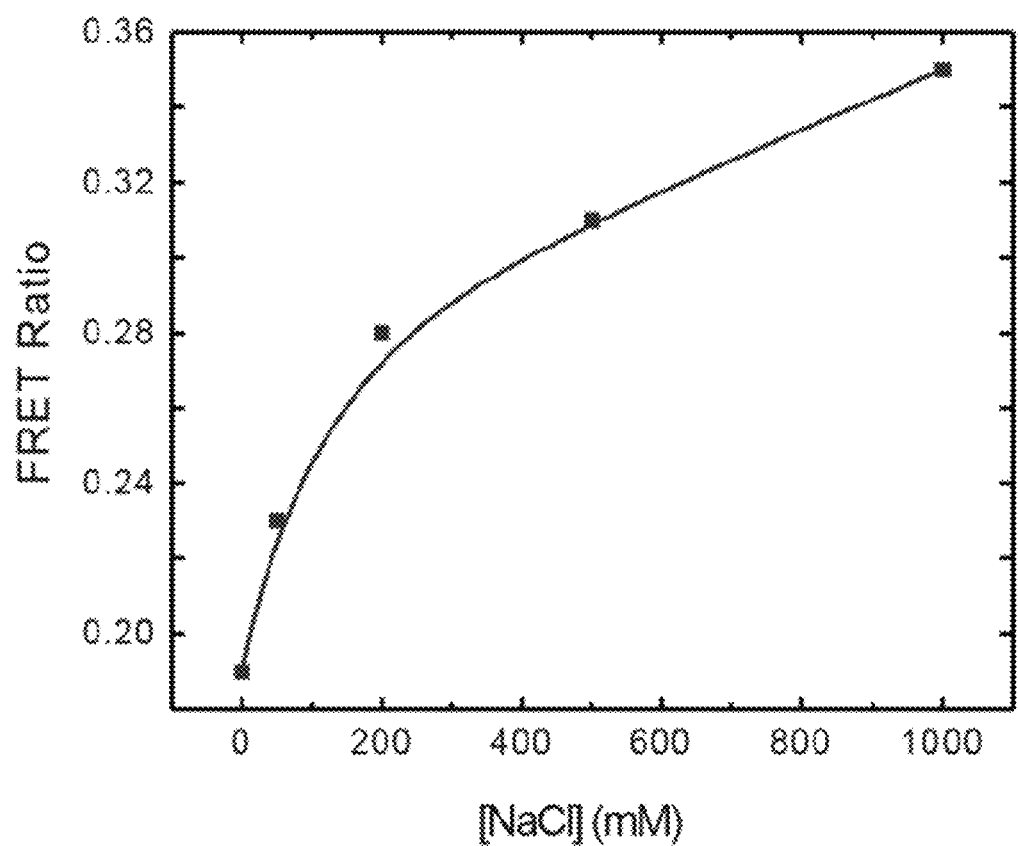
FIG. 12 shows a sensor of the present disclosure is sensitive to changes in salt concentration.

The flexible molecular sensor is sensitive to changes in salt concentration (FIG. 12). Given that DNA is negatively charged in physiological buffer, the two arms experience repulsion. Increasing the salt concentration in the buffer provides the counter-ions that can screen the negative charge of the DNA, and therefore reduce the repulsion bringing the arms closer to each other on average. The FRET ratio therefore increases.

Figure 13:
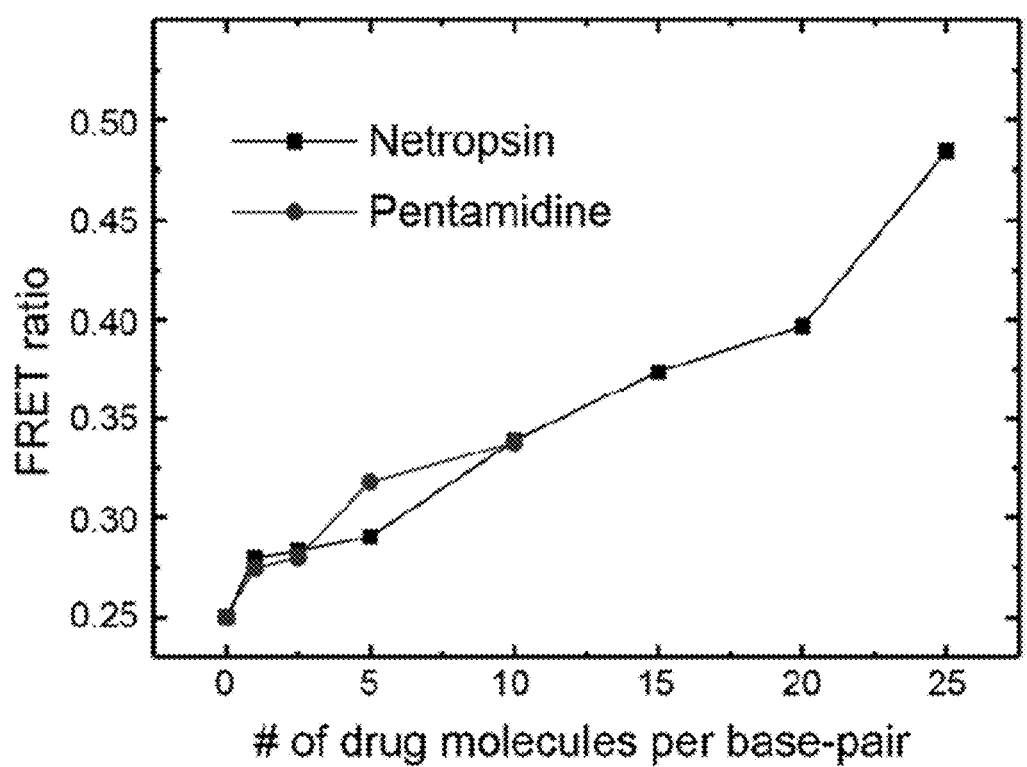
FIG. 13 shows a sensor of the present disclosure is sensitive to groove binders.

The flexible molecular sensor is sensitive to groove binders (FIG. 13). Many groove binders interact with DNA primarily electrostatically given that they are positively charged. Therefore, upon binding DNA they screen the negative charge and bring the double-stranded arms closer together and increase the FRET ratio. Two examples of groove binding drugs are shown in the figure where the FRET ratio measure in solution increases with drug concentration.

Figure 14:
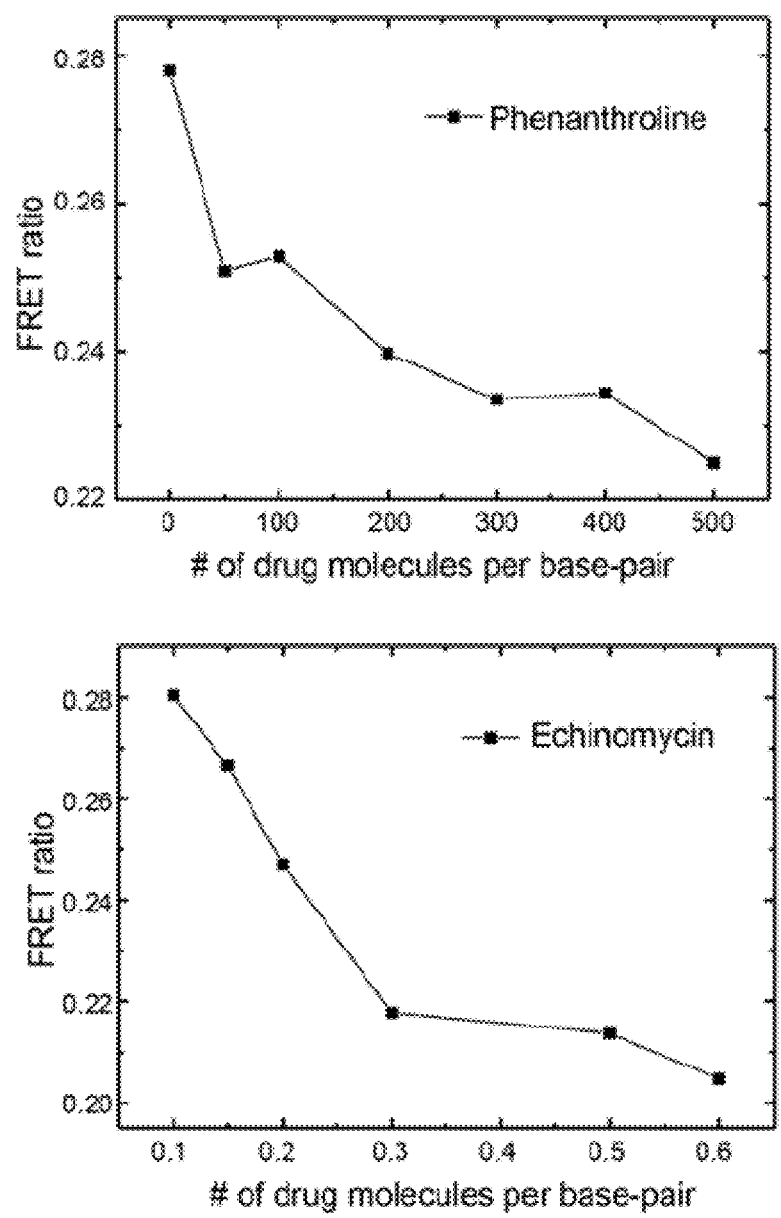
FIG. 14 shows a sensor of the present disclosure is sensitive to intercalators.

The flexible molecular sensor is sensitive to intercalators (FIG. 14). Intercalators bind DNA by wedging between the base pairs of double-stranded DNA. In doing so, they increase the length of DNA. Therefore, incubating the tongs-shaped sensor with intercalators increases the lengths of the arms. For the same bending angle of the sensor, the FRET pair will then become further apart reducing the FRET ratio. The figure shows examples for two intercalating molecules where the FRET ratio becomes smaller with increasing intercalator concentration.

EXAMPLE 4

This example provides a description of using linear molecular sensors of the present disclosure.

FIG. 15 shows a schematic of the dsDNA based intercalaor linear molecular sensor. Each strand of the DNA is labelled at the 5'-end, one with Cy3 which acts as the donor and the other with Cy5 which acts as the acceptor of a FRET pair. As intercalating molecules (blue) wedge between the dsDNA bases (bottom image), the contour length of the DNA increases compared to the native DNA (top image) and the distance between donor and acceptor molecules increases reducing the FRET efficiency.

Figure 16:
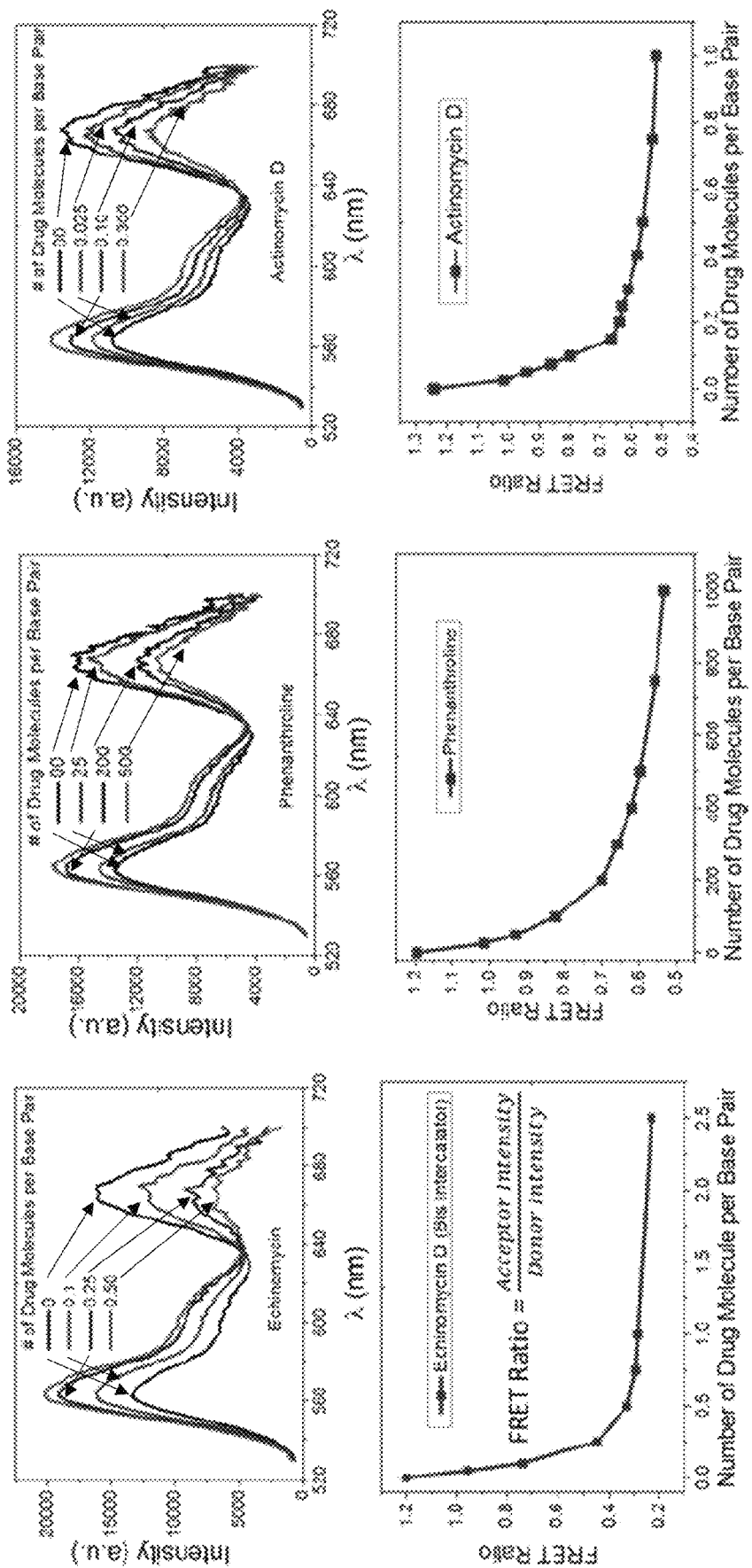
FIG. 16 shows examples of the linear sensor detecting intercalating molecules in a concentration-dependent manner.

Examples of the linear sensor detecting intercalating molecules in a concentration-dependent manner are shown in FIG. 16. Incubating the sensor in a solution of increasing concentration of intercalating molecules increases the number of molecules wedging between the bases thus increasing the distance between the donor and acceptor and reducing the efficiency of energy transfer. This is observed as an increase in the fluorescence of Cy5 (at 670 nm) and a concomitant decrease in the fluorescence of Cy3 (at 570 nm). The spectra shown in the top row were measured on a plate reader by exciting the donor (Cy3) at 500 nm and recording the spectra in solutions containing three different intercalating molecules as indicated on each figure (Echinomycin, Phenanthroline, and Actinomycin D). The bottom row shows the FRET ratio (measured as the ratio of acceptor:donor peak intensities) as a function of the concentration of each intercalating drug molecule expressed as the number of molecules per base pair of the sensor in solution. These measurements provide information on the interaction of the molecule with DNA as well as binding kinetics.

Figure 17:
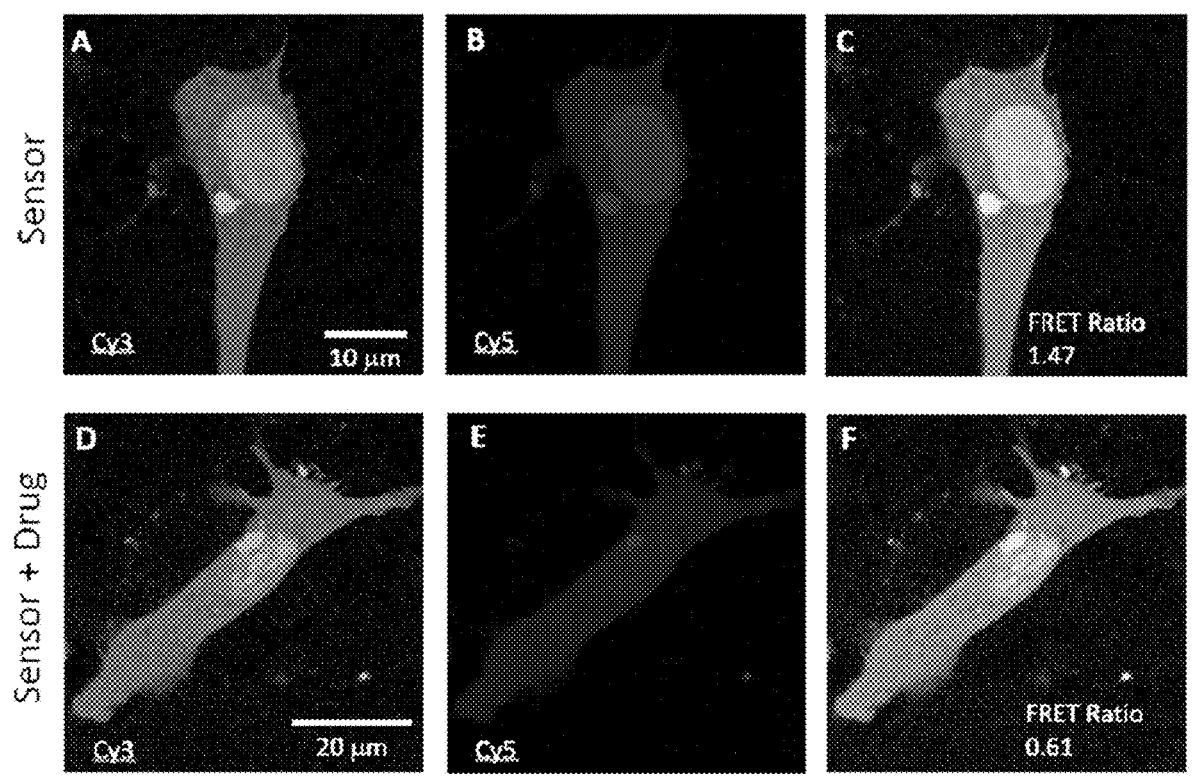
FIG. 17 shows a linear sensor of the present disclosure can report on the interaction of intercalating molecules with DNA within living cells.
Figure 18:
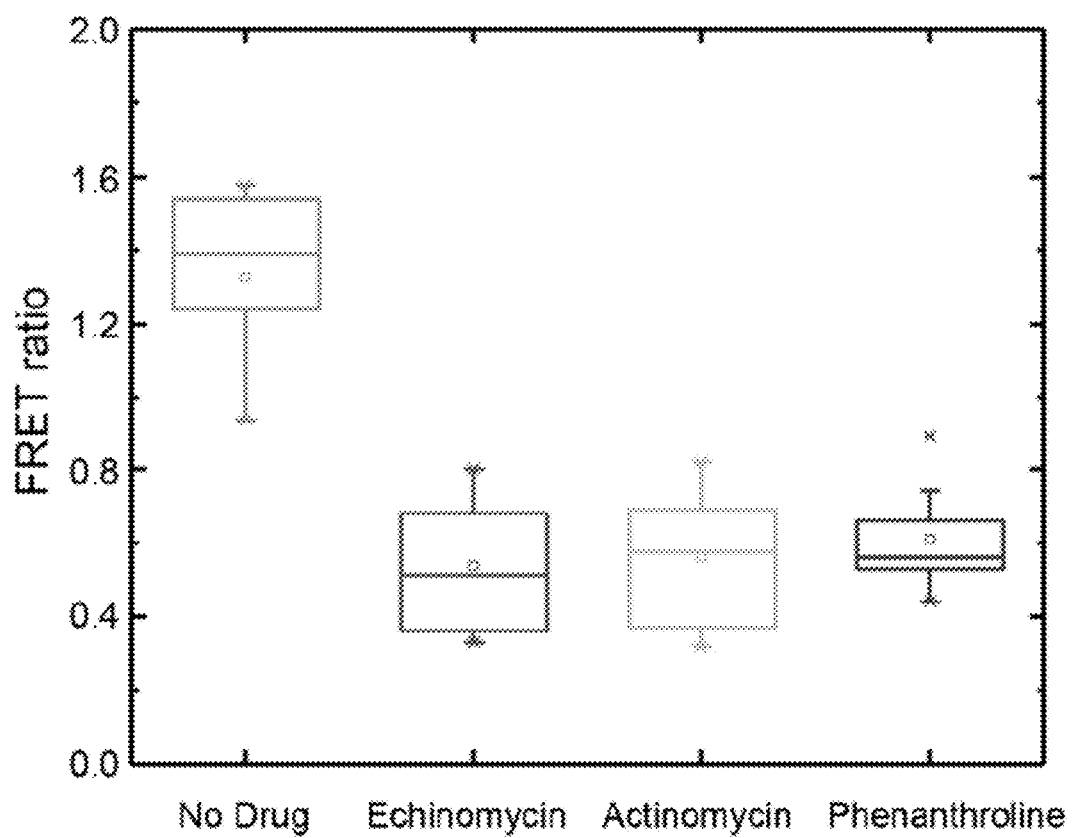
FIG. 18 shows three examples illustrating the use of the sensor to detect the DNA-drug interaction within cells.

The linear sensor can report on the interaction of intercalating molecules with DNA within living cells (FIG. 17). The linear sensor readily enters cells in culture by liposome transfection and distributes within the cytosol and nucleus. Using laser scanning confocal microscopy the cells are imaged by exciting the donor (Cy3) and imaging the fluorescence of Cy3 and Cy5 (acceptor) in the appropriate spectral ranges (images A, B, D, E). The false-colored images can be merged therefore producing a false color image where green indicates a small FRET ratio and red a large FRET ratio and intermediate values being yellow/orange (images C and F). As expected, introducing the intercalating drug molecule (Actinomycin D) in the culture medium and its uptake by the cells leads to its binding to the sensor and a decrease in the FRET ratio (image F) compared to cells with no Drug (image C). The FRET ratio can be measured from the ratio of Cy5:Cy3 intensities. This assay can be used to measure drug entry in cells in vitro and can also be adapted for in vivo drug uptake detection. It can further be used to follow the dynamics of drug entry or clearing.

Three examples illustrating the use of the linear molecular sensor to detect the DNA-drug interaction within cells are shown in FIG. 17. As illustrated in FIG. 17, drug entry into the cells can be imaged by virtue of its binding to the sensor internalized within the cell. The FRET ratio decreases when the drug binds to the DNA. The figure illustrates the clear difference in FRED ratio between groups of cells in the absence of intercalating drugs and those in the presence of one of three intercalating drugs: Echinomycin, Actinomycin D, or Phenanthroline.

Figure 19:
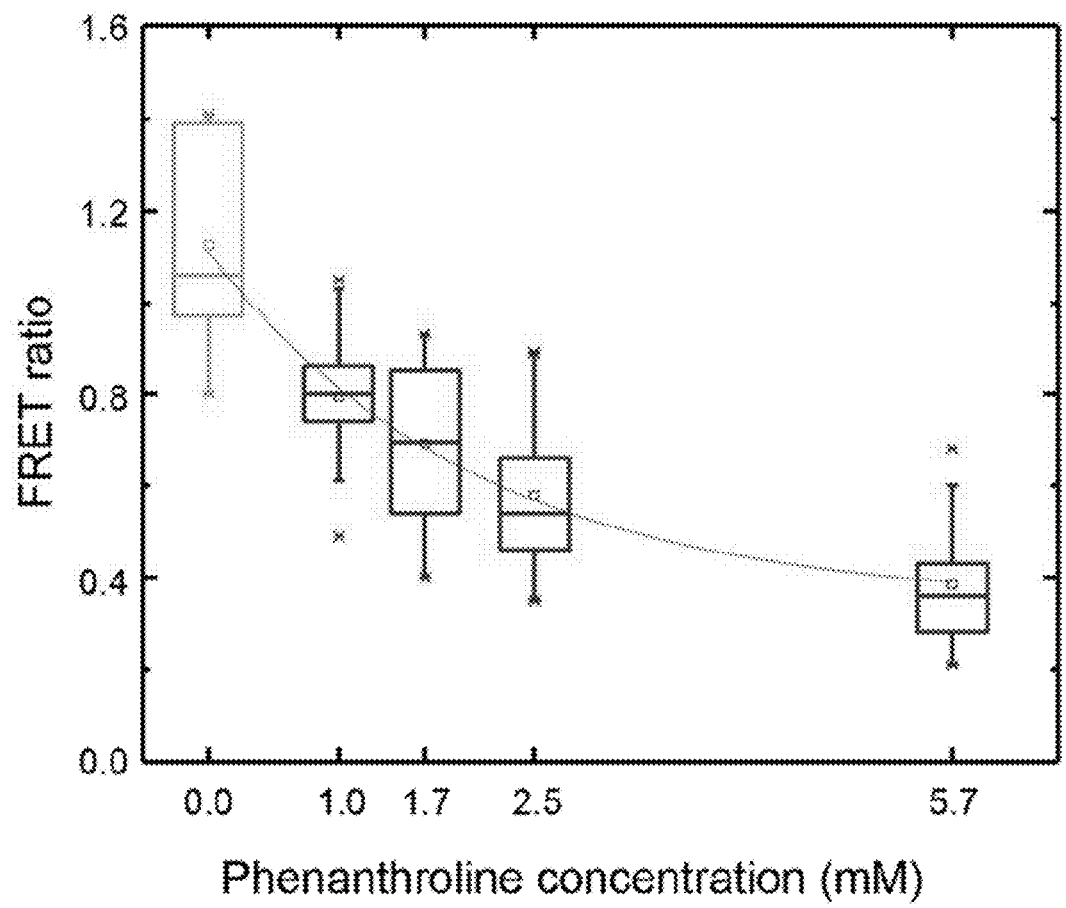
FIG. 19 shows a sensor of the present disclosure can detect the amount of drug in the cell culture medium.

The linear molecular sensor can detect the amount of drug in the cell culture medium (FIG. 19). Cells were imaged in culture medium or culture medium supplemented with various concentrations of phenanthroline. The FRET ratio was measured from the images as described in FIG. 17 for 9-45 cells for each concentration. Small changes in the drug concentration produce distinct sensor responses (FRET ratio).

Figure 20:
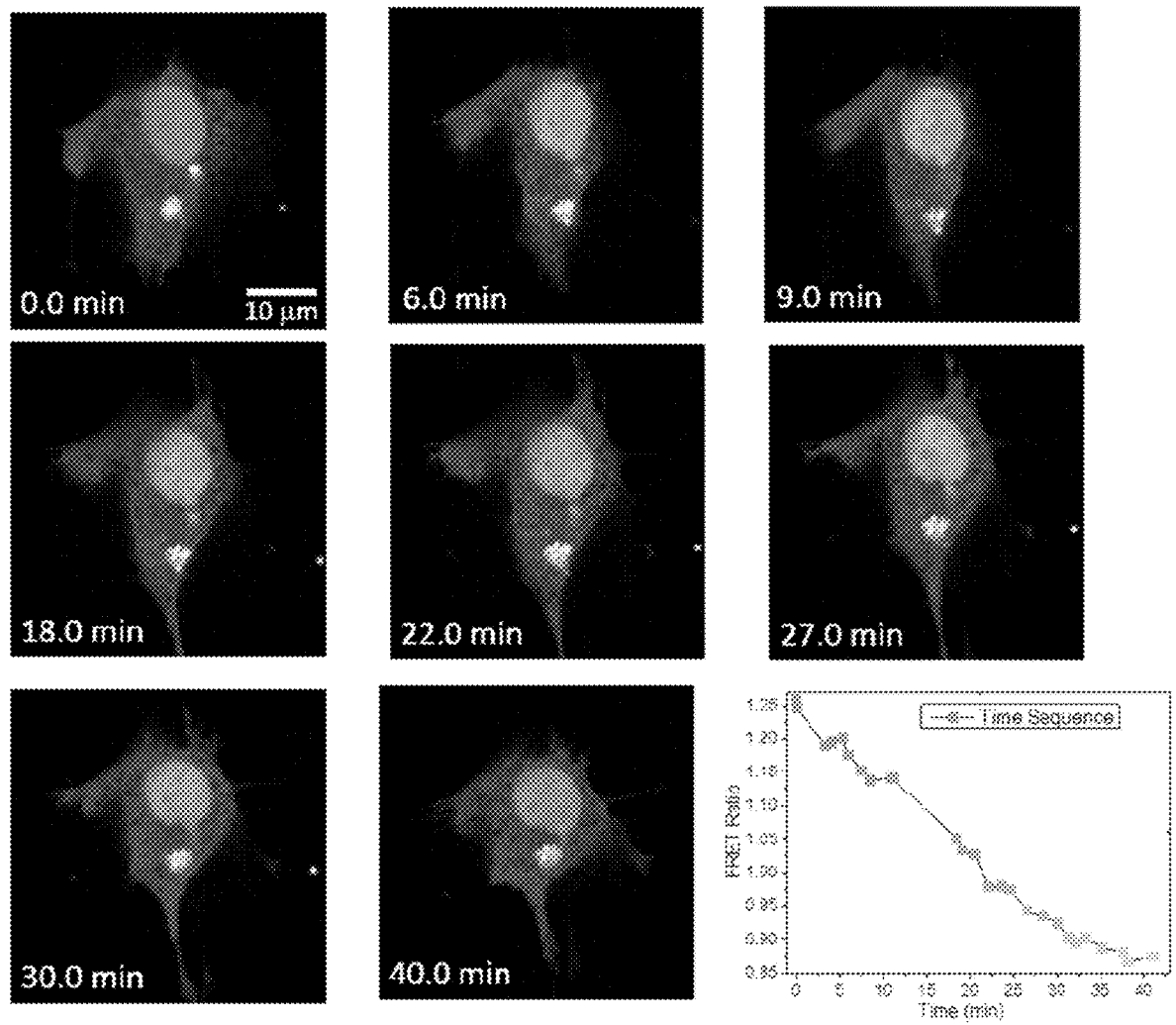
FIG. 20 shows a sensor of the present disclosure can detect the time course of drug entry and diffusion within the cells.

The linear molecular sensor can detect the time course of drug entry and diffusion within the cells (FIG. 20). Cells were transfected with the sensor and imaged in culture medium as described in FIG. 17. Merged images produced by overlaying the Cy3 and Cy5 channels are shown here at different time points after supplementing the medium with the intercalating drug Actinomycin D. With increasing time, the color of the cell in the merged images turns from orange (high FRET) to green (low FRET). A low FRET ratio indicates that a large amount of the drug binds the DNA and extends the sensor. The average FRET ratio measured as Cy5:Cy3 intensities in the images is plotted as a function of time in the lower right panel. This proof of principle experiment demonstrates that the sensor can be used to detect—at the single cell or subcellular level—the efficacy of drug entry into the cell as well as the time course of it's binding to the DNA.

EXAMPLE 5

This example provides a description of using linear molecular sensors of the present disclosure.

Figure 22:
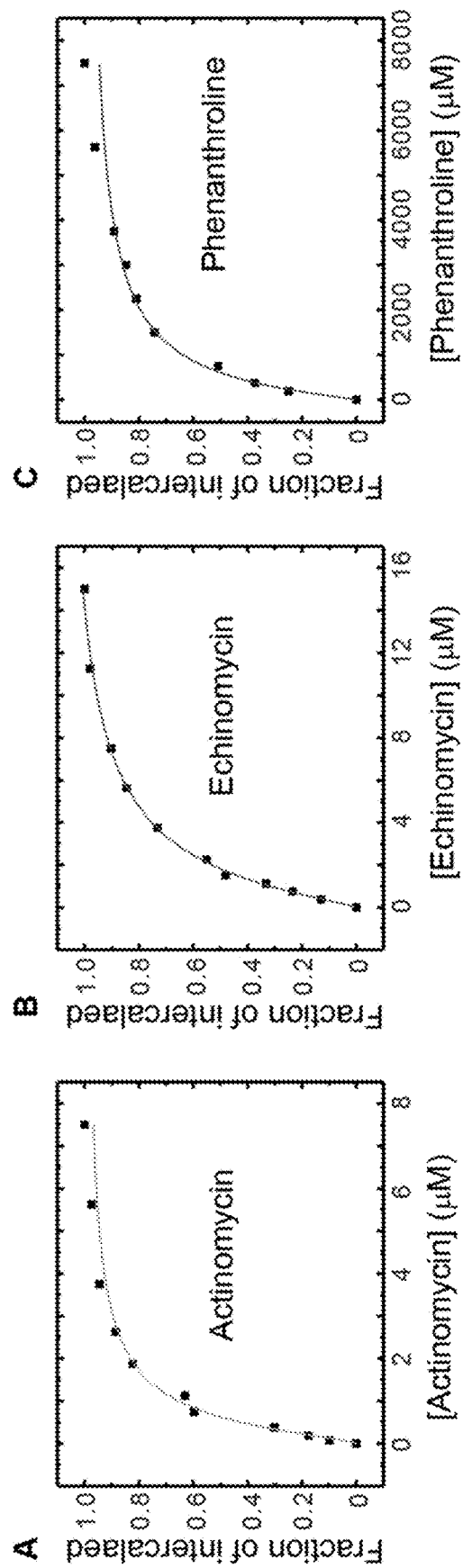
FIG. 22 shows an oligonucleotide probe of the present disclosure can be used to measure the binding constant of the intercalating drug. The data in FIGS. 21D, 21F, and 21H were used to plot the fraction of intercalated bases in the probe as a function of the drug concentration for Actinomycin (A), Echinomycin (B), and Phenathroline (C), assuming all binding sites were occupied at saturation. The data was fitted with a Hill plot to extract the binding constant from the fit parameters and was found to be $2 \times 10^6$ M$^-$, $0.4 \times 10^6$ M$^{-1}$, and 710 M$^{-1}$ for Actinomycin, Echinomycin, and Phenonthraline, respectively.
Figure 23:
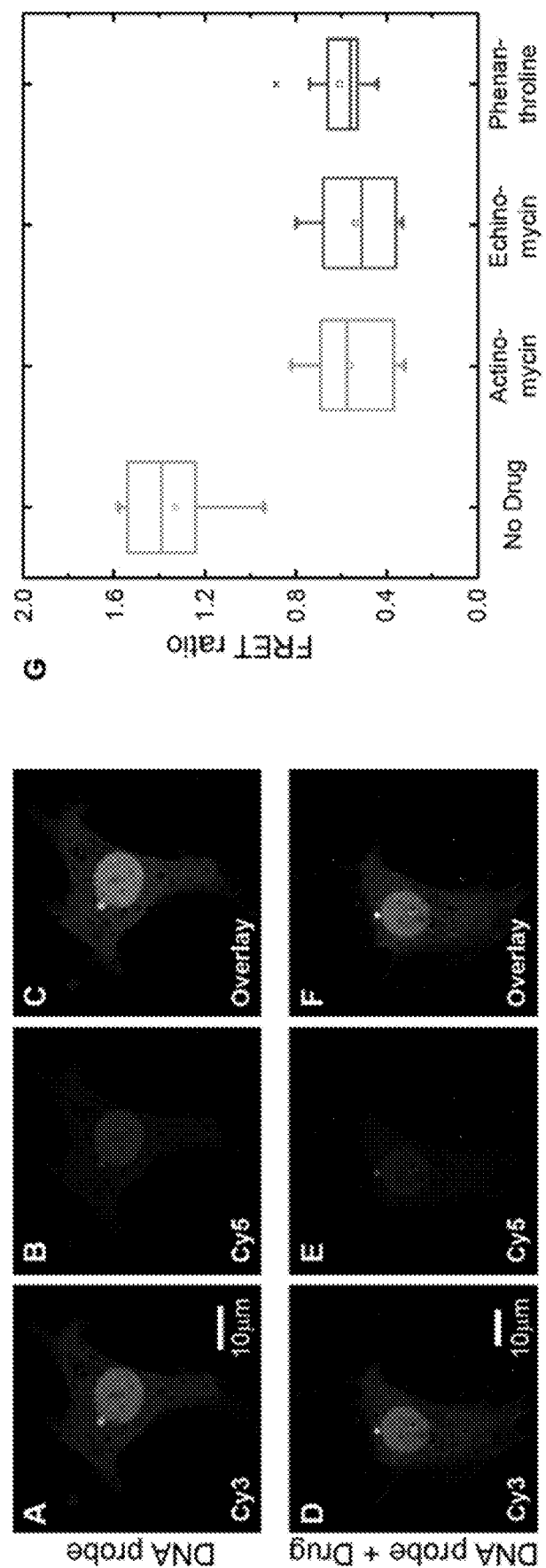
FIG. 23 shows a linear probe can detect intercalating molecules in living cells and follow their binding dynamics. Cells transfected with the oligo probe were imaged by exciting the donor (Cy3) and imaging the fluorescence of Cy3 (A) and Cy5 (acceptor) (B) in the appropriate spectral ranges using a confocal microscope. (C) The false-colored images can be merged, therefore producing a false color image where orange indicates a large FRET ratio. When transfected cells are imaged in the presence of Actinomycin in the culture medium, Cy5 intensity (E) drops relative to that of Cy3 (D) resulting in a green merged image (F) due to the drop if the FRET efficiency upon intercalation within the cell. (G) The drop in the FRET ratio is measured by calculating the ratio of the Cy5 signal to that of Cy3 within the nuclei of cells in presence of the three intercalating compounds. The extent of FRET ratio drop depends on the concentration of the compound in the culture medium (H-I) showing sensitivity over an order of magnitude of concentration. (J-L) The time-lapse images on the left of each panel show overlays similar to (C) and (F) recorded just after the drug was introduced into the culture medium to follow the time-course of its entry into the cell. The drug enters the cell within minutes and is detected as a drop in the FRET ratio of the probe within the nucleus as quantified in the graphs for each drug.
Figure 23:
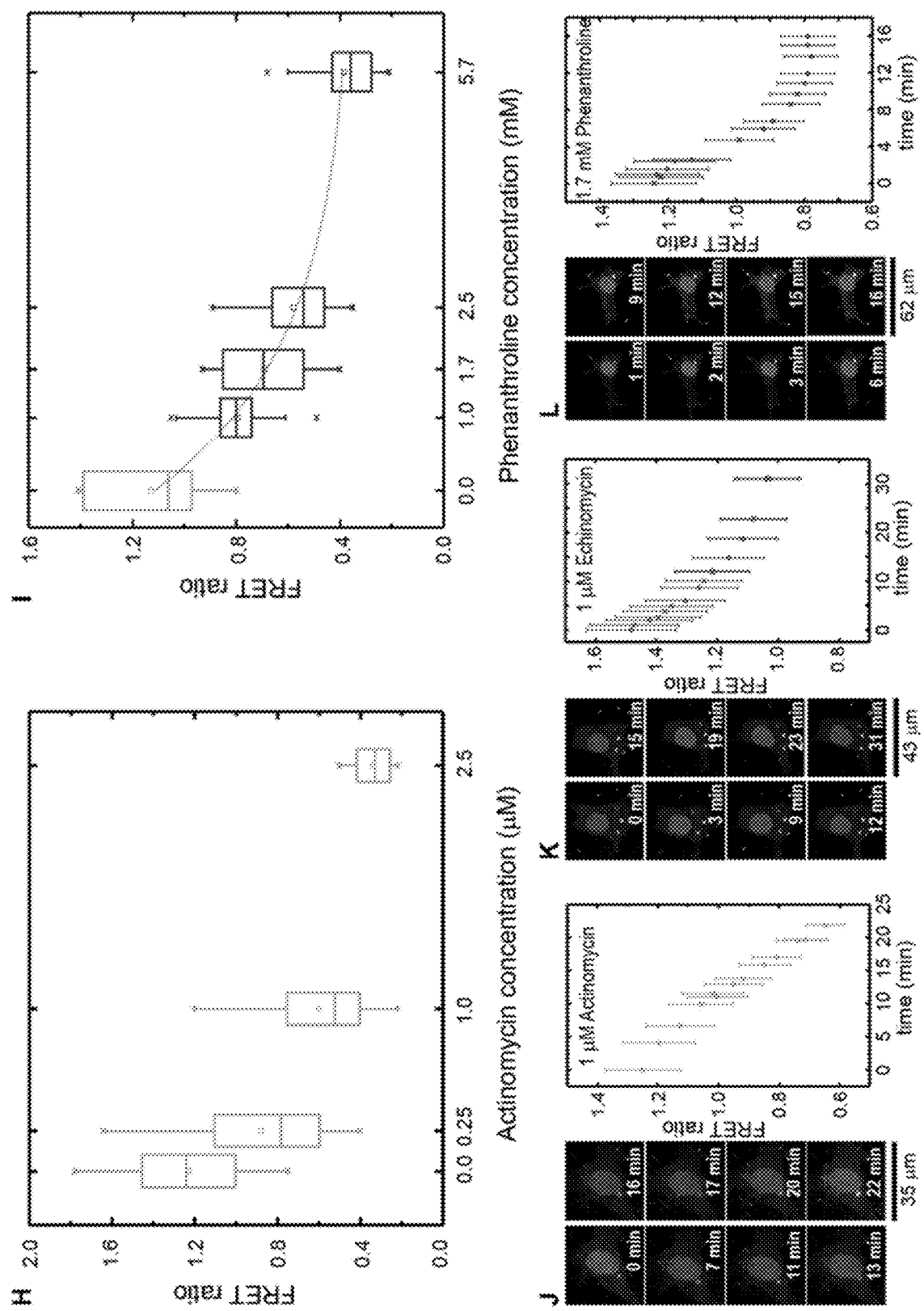
Figure 24:
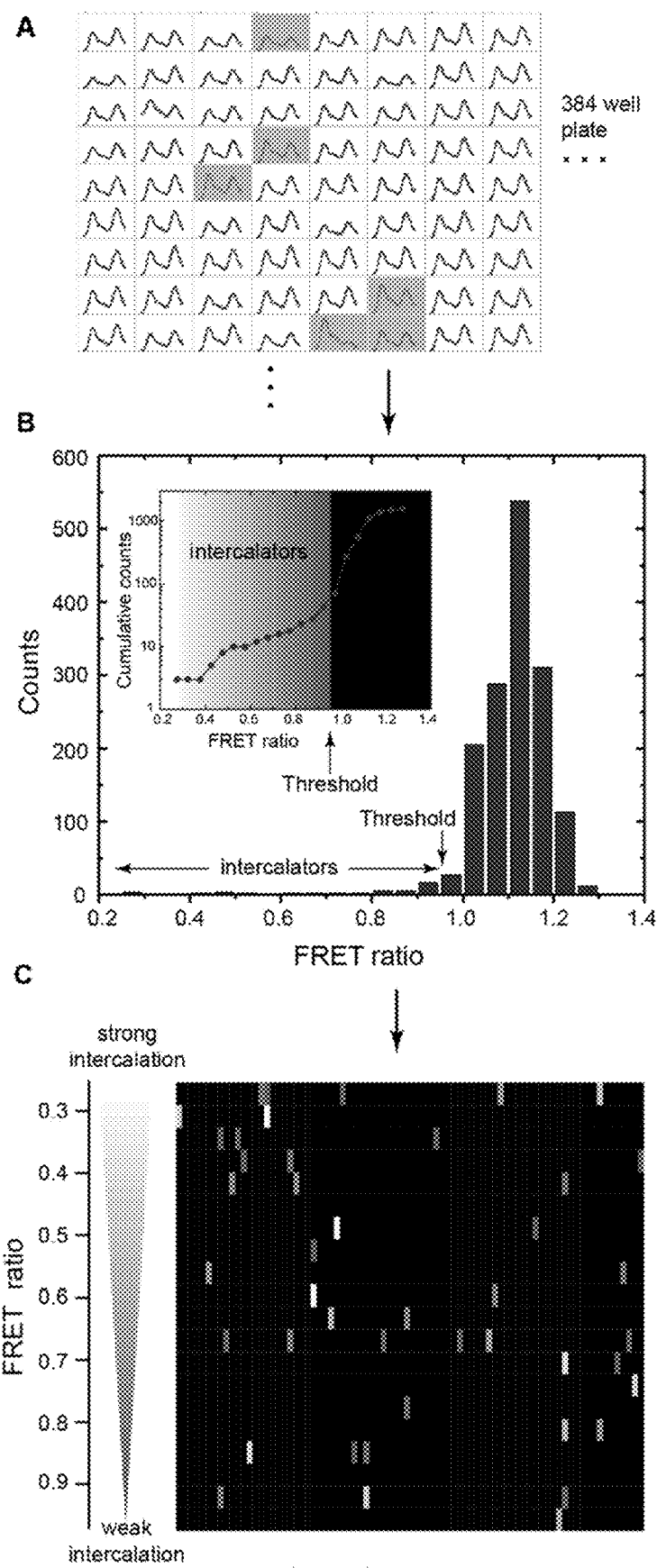
FIG. 24 shows a linear probe is used in a high-throughput format for intercalating drug discovery. A library of compounds was mixed with the oligo probe in 384 well plate format. (A) The fluorescence spectra of the probe were recorded on a plate reader as in FIG. 21 and the FRET ratio (Cy5/Cy3 intensity) was calculated. Hits where the FRET ratio drops compared to control wells and where the compound is not fluorescent in the absence of the probe are highlighted. (B) A library consisting of 1600 compounds from FDA and internationally approved drugs was screened to detect potential intercalators that can be drug repositioning targets. The distribution of FRET ratios shows a peak at ~1.1 indicating that most drugs do not intercalate DNA. However, the tail of the distribution includes 44 drugs that result in a small FRET ratio (more than three standard deviations away from the peak). The inset shows the cumulative distribution on a logarithmic scale for clarity. (C) The heat map shows all 1600 drugs where wells with a FRET ratio above the threshold are blackened out to emphasize the range of FRET ratios of the identified intercalators.

FIG. 21 shows a linear sensor of the present disclosure is sensitive to intercalating molecules in a concentration-dependent manner. FIG. 22 shows a linear sensor of the present disclosure can be used to measure the binding constant of an intercalating drug. FIG. 23 shows a linear sensor of the present disclosure can detect intercalating molecules in living cells and follow their binding dynamics. FIG. 24 shows a linear sensor of the present disclosure used in a high throughput format for intercalating drug discovery.

EXAMPLE 6

This example provides examples of compounds identified as intercalators via methods of the present disclosure utilizing linear molecular sensors of the present disclosure.

TABLE 1

Molecules identified as intercalators by using a method of the present disclosure.

| FRET ratio | Molecular Name | CAS # | Formula |
| --- | --- | --- | --- |
| 0.47652977 | DACTINOMYCIN | 50-76-0 | $C_{62}H_{86}N_{12}O_{16}$ |
| 0.7057226 | AMILORIDE HYDROCHLORIDE | 17440-83-4, 2016-88-8 [anhydrous], 2609-46-3 [amiloride] | $C_6H_9Cl_2N_7O$ |
| 0.83333532 | AMODIAQUINE DIHYDROCHLORIDE | 6398-98-7, 69-44-3 [anhydrous], 86-42-0 [amodiaquine] | $C_{20}H_{24}Cl_3N_3O$ |
| 0.13747821 | MODALINE SULFATE | 2856-75-9 | $C_{10}H_{17}N_3O_4S$ |
| 0.92283782 | APOMORPHINE HYDROCHLORIDE | 41372-20-7, 314-19-2 [anhydrous], 58-00-4 [apomorphine] | $C_{17}H_{18}ClNO_2$ |
| 0.92123571 | ETHYL VANILLIN | 121-32-4 | $C_9H_{10}O_3$ |
| 0.7832403 | BENSERAZIDE HYDROCHLORIDE | 322-35-0 | $C_{10}H_{16}ClN_3O_5$ |
| 0.91315582 | PROPRANOLOL HYDROCHLORIDE (+/−) | 318-98-9, 525-66-6 [propranolol] | $C_{16}H_{22}ClNO_2$ |
| 0.90514632 | GEMIFLOXACIN MESYLATE | 204519-65-3 | $C_{19}H_{24}FN_5O_7S$ |
| 0.44299798 | TILORONE | 27591-69-1, 27591-97-5 [tilorone] | $C_{25}H_{34}N_2O_3$ |
| 0.84804312 | CHLOROQUINE DIPHOSPHATE | 50-63-5 | $C_{18}H_{32}ClN_3O_8P_2$ |
| 0.29186646 | ACRISORCIN | 7527-91-5 | $C_{25}H_{28}N_2O_2$ |
| 0.91868899 | OCTOCRYLENE | 6197-30-4 | $C_{24}H_{27}NO_2$ |
| 0.81801629 | PRAZOSIN HYDROCHLORIDE | 19237-84-4, 19216-56-9 [prazosin] | $C_{19}H_{22}ClN_5O_4$ |
| 0.86181446 | PRIMAQUINE PHOSPHATE | 63-45-6, 90-34-6 [primaquine] | $C_{15}H_{27}N_3O_9P_2$ |

TABLE 1-continued

Molecules identified as intercalators by using a method of the present disclosure.

| FRET ratio | Molecular Name | CAS # | Formula |
| --- | --- | --- | --- |
| 0.77314694 | GUANABENZ ACETATE | 23256-50-0 | $C_{10}H_{12}Cl_2N_4O_2$ |
| 0.27432512 | QUINACRINE HYDROCHLORIDE | 6151-30-0, 69-05-6 [anhydrous], 83-89-6 [quinacrine] | $C_{23}H_{32}Cl_3N_3O$ |
| 0.93328183 | QUINIDINE GLUCONATE | 7054-25-3, 6591-63-5 [quinidine sulfate], 56-54-2 [quinidine] | $C_{26}H_{36}N_2O_9$ |
| 0.60674609 | TACRINE HYDROCHLORIDE | 1684-40-8 | $C_{13}H_{15}ClN_2$ |
| 0.29409213 | AMINACRINE | 90-45-9, 134-50-9 [aminacrine hydrochloride] | $C_{13}H_{10}N_2$ |
| 0.91837672 | PROGESTERONE | 57-83-0 | $C_{21}H_{30}O_2$ |
| 0.93382254 | METHOXSALEN | 298-81-7 | $C_{12}H_8O_4$ |
| 0.45663699 | HYCANTHONE | 3105-97-3 | $C_{20}H_{24}N_2O_2S$ |
| 0.87894961 | NAPHAZOLINE HYDROCHLORIDE | 550-99-2, 835-31-4 [naphazoline] | $C_{14}H_{15}ClN_2$ |
| 0.0987606 | SODIUM NITROPRUSSIDE | 13755-38-9 | $C_5FeN_6Na_2O$ |
| 0.90859129 | CARVEDILOL | 72956-09-3 | $C_{24}H_{26}N_2O_4$ |
| 0.14891898 | SYMCLOSENE | 87-90-1 | $C_3Cl_3N_3O_3$ |
| 0.89928784 | METHYSERGIDE MALEATE | 129-49-7 | $C_{25}H_{31}N_3O_6$ |
| 0.80367708 | ACEPROMAZINE MALEATE | 3598-37-6 | $C_{23}H_{26}N_2O_5S$ |
| 0.94951692 | PERPHENAZINE | 58-39-9 | $C_{21}H_{26}ClN_3OS$ |
| 0.9092936 | ACETOPHENAZINE MALEATE | 5714-00-1 | $C_{27}H_{33}N_3O_6S$ |
| 0.6784301 | ALFUZOSIN HYDROCHLORIDE | 81403-80-7 | $C_{19}H_{28}ClN_5O_4$ |
| 0.80887631 | DOXAZOSIN MESYLATE | 77883-43-3 | $C_{24}H_{29}N_5O_8S$ |
| 0.6995613 | CISPLATIN | 15663-27-1 | $H_6Cl_2N_2Pt$ |
| 0.94634079 | CARVEDILOL PHOSPHATE | 610309-89-2 | $C_{24}H_{29}N_2O_8P$ |
| 0.51256099 | CHLORPYRIFOS | 2921-88-2 | $C_9H_{11}Cl_3NO_3PS$ |
| 0.74468514 | OLTIPRAZ | 64224-21-1 | $C_8H_6N_2S_3$ |
| 0.45100475 | GUANIDINE HYDROCHLORIDE | 50-01-1 | $CH_7Cl_2N_3$ |
| 0.33249441 | PYRONARIDINE TETRAPHOSPHATE | 76748-86-2 | $C_{29}H_{44}ClN_5O_{18}P_4$ |
| 0.72275176 | TROPISETRON HYDROCHLORIDE | 105826-92-4, 89565-68-4 | $C_{17}H_{21}ClN_2O_2$ |
| 0.61262307 | DEQUALINIUM CHLORIDE | 522-51-0, 6707-58-0 [dequalinium] | $C_{30}H_{40}Cl_2N_4$ |
| 0.42623633 | BERBERINE CHLORIDE | 633-65-8, 2086-83-1 | $C_{20}H_{18}ClNO_4$ |
| 0.77194634 | ALOIN | 5133-19-7 | $C_{21}H_{22}O_{10}$ |
| 0.70004042 | DIACERIN | 13739-02-1 | $C_{19}H_{12}O_8$ |
| 0.74942885 | KHELLIN | 82-02-0 | $C_{14}H_{12}O_5$ |
| 0.39851788 | CHLORAMINE-T | 127-65-1 | $C_7H_7ClNNaO_2S$ |
| 0.75122104 | HYDROQUINIDINE | 1435-55-8 | $C_{20}H_{26}N_2O_2$ |
| 0.386671 | HARMOL HYDROCHLORIDE | 40580-83-4 | $C_{12}H_{11}ClN_2O$ |
| 0.728834 | DICTAMNINE | 484-29-7 | $C_{12}H_9NO_2$ |
| 0.422789 | LINAMARIN | 554-35-8 | $C_{10}H_{17}NO_6$ |
| 0.514094 | PALMATINE CHLORIDE | 10605-02-4 | $C_{21}H_{22}ClNO_4$ |
| 0.727752 | COTARNINE CHLORIDE | 10018-19-6, 82-54-2 [cotarnine] | $C_{12}H_{14}ClNO_3$ |
| 0.645994 | HARMALINE | 304-21-2 | $C_{13}H_{14}N_2O$ |
| 0.37999 | LUPEOL ACETATE | 1617-68-1 | $C_{32}H_{52}O_2$ |
| 0.37999 | N,N-HEXAMETHYLENEAMILORIDE | | $C_{12}H_{18}ClN_7O$ |
| 0.613353 | HAEMATOXYLIN PENTAACETATE | | $C_{26}H_{24}O_{12}$ |
| 0.838533 | CHRYSIN DIMETHYL ETHER | 21392-57-4 | $C_{17}H_{14}O_4$ |
| 0.585184 | HARMANE | 486-84-0 | $C_{12}H_{10}N_2$ |
| 0.826916 | 2,2'-AZO-bis-2-AMINOPROPANE | 2997-92-4 | $C_8H_{20}Cl_2N_6$ |
| 0.936374 | PLUMBAGIN | 481-42-5 | $C_{11}H_8O_3$ |
| 0.681741 | RHOIFOLIN | 17306-46-6 | $C_{27}H_{30}O_{14}$ |
| 0.754016 | HARMINE | 442-51-3 | $C_{13}H_{12}N_2O$ |
| 0.543032 | 4'-METHOXYFLAVONE | 4143-74-2 | $C_{16}H_{12}O_3$ |
| 0.676053 | RUTILANTINONE | 21288-61-9 | $C_{22}H_{20}O_9$ |

The screen included a handful of known intercalating drugs such as Actinomycin, which confirms the sensitivity of the method. Moreover, many drugs that were not previously reported as intercalators were identified in the screen and may be used for conditions not previously indicated.

EXAMPLE 7

This example provides a description of using flexible molecular sensors of the present disclosure.

Figure 25:
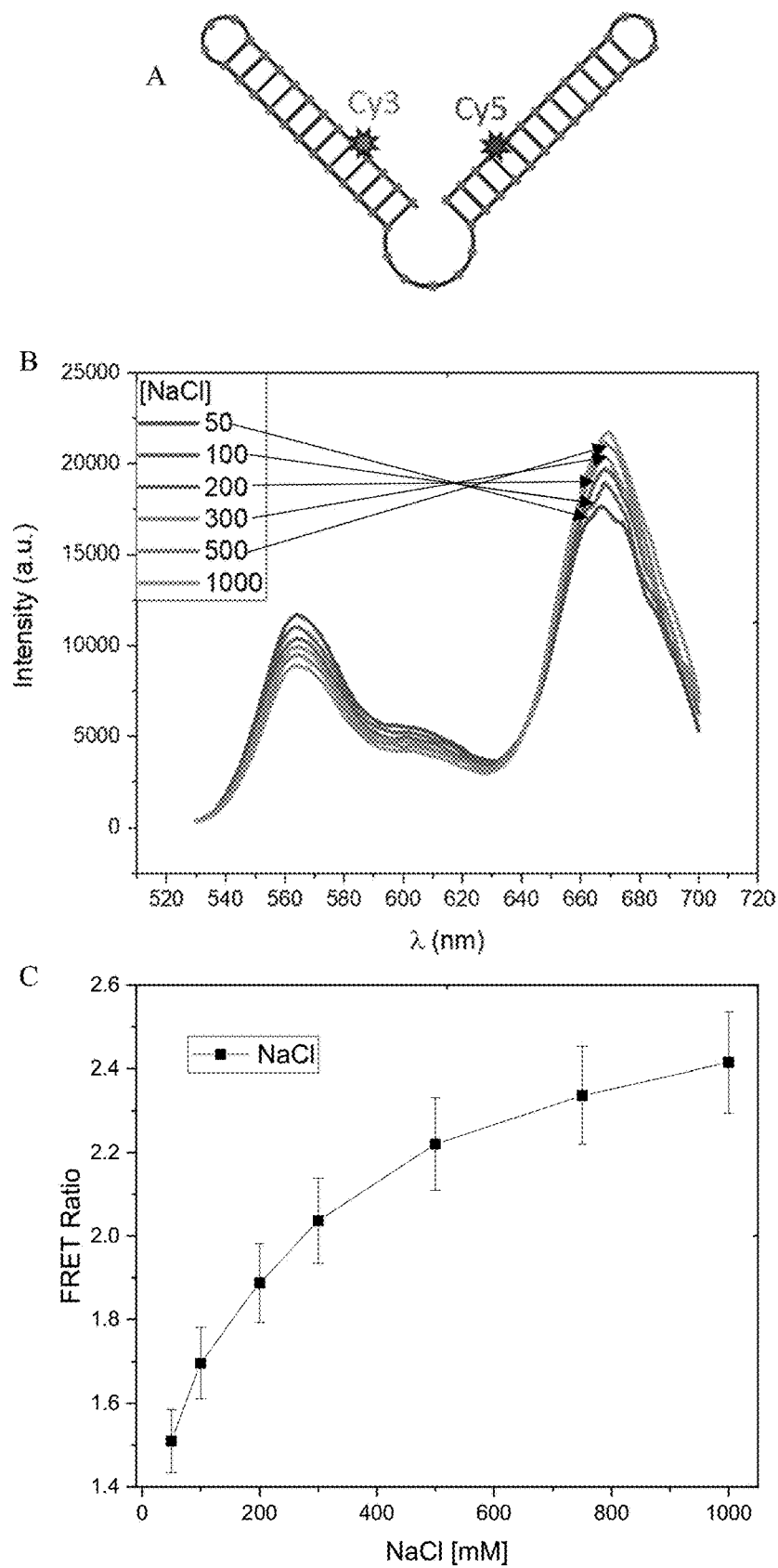
FIG. 25 shows the arms of the tongs-shaped oligonucleotide probe (flexible molecular sensor) get closer with increased electrostatic screening. A) The single stranded oligonucleotide is designed to hybridize forming two stiff double-stranded arms separated by a single stranded linker. The linker renders the sensor flexible in the middle allowing it to bend. A change in the average bending of the sensor will also change the distance between the fluorophores (Cy3 and Cy5) labelling the sensor at the base of the double-stranded arms, and therefore change the FRET efficiency between the fluorophores. (B) Fluorescence spectra of the sensor excited at a wavelength of 500 nm show a reduced donor fluorescence (570 nm) and increased acceptor fluorescence (670 nm) as the NaCl concentration is increased. (C) The ratio of peak acceptor/peak donor fluorescence intensity (FRET ratio) is calculated to characterize the extent of energy transfer. The FRET ratio increases with NaCl concentration indicating that the salt ions shield electrostatic repulsion between the sensor arms making them more likely to come closer together.
Figure 26:
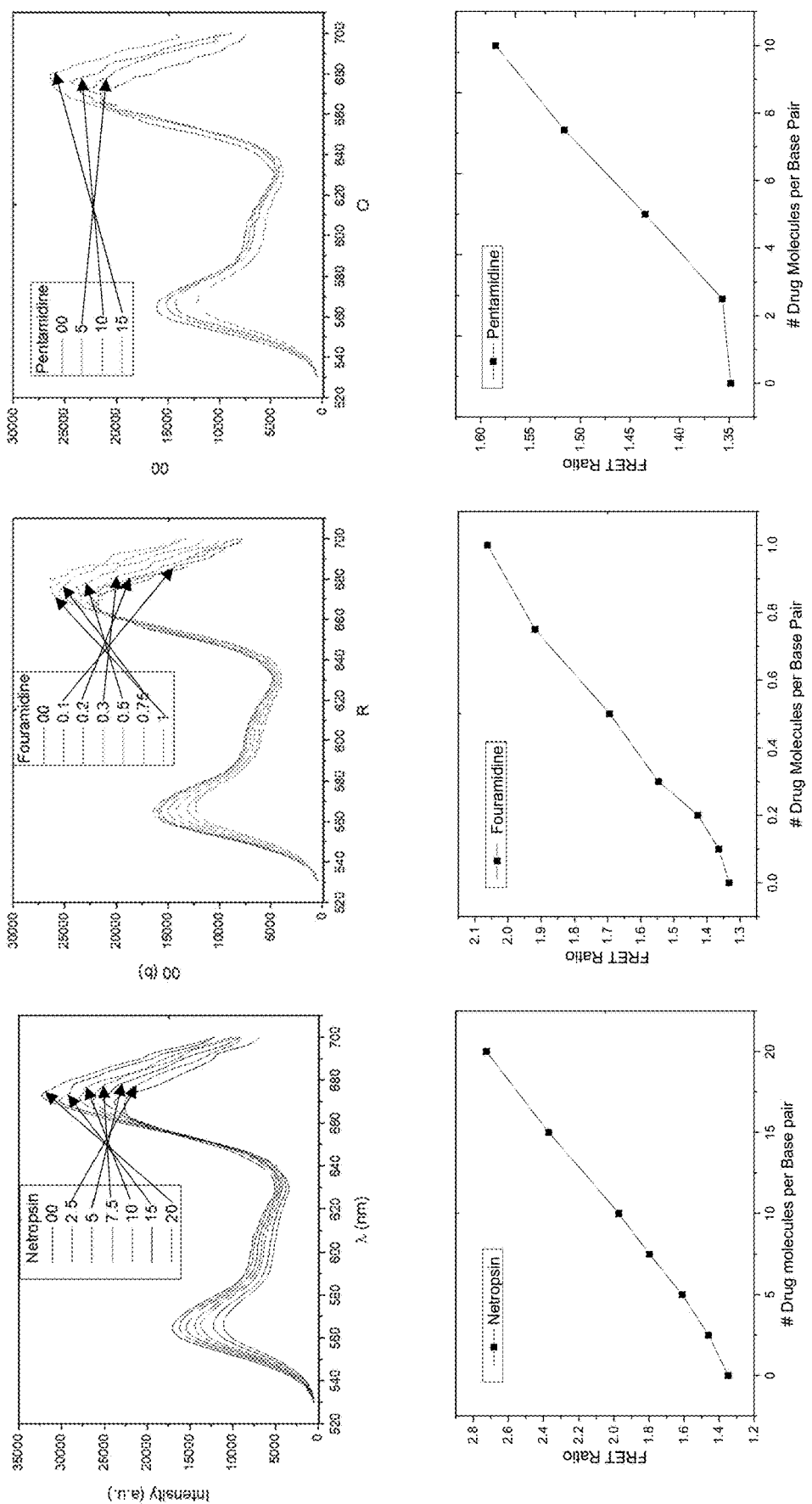
FIG. 26 shows groove-binding compounds are detected by the sensor as a concentration-dependent increase of the FRET ratio. Spectra (top) and FRET ratio measurements (bottom) measured for the sensor in the presence of three groove-binding compounds at various concentrations (left-to-right: Netrospin, Fourmadine, and Pentamidine). The increase in the FRET ratio indicates that the sensor arms come closer together which would be expected if the molecules binding the DNA groove is electrostatic in nature, and therefore, like salt ions would shield the negatively charged sensor arms making them repel less.
Figure 27:
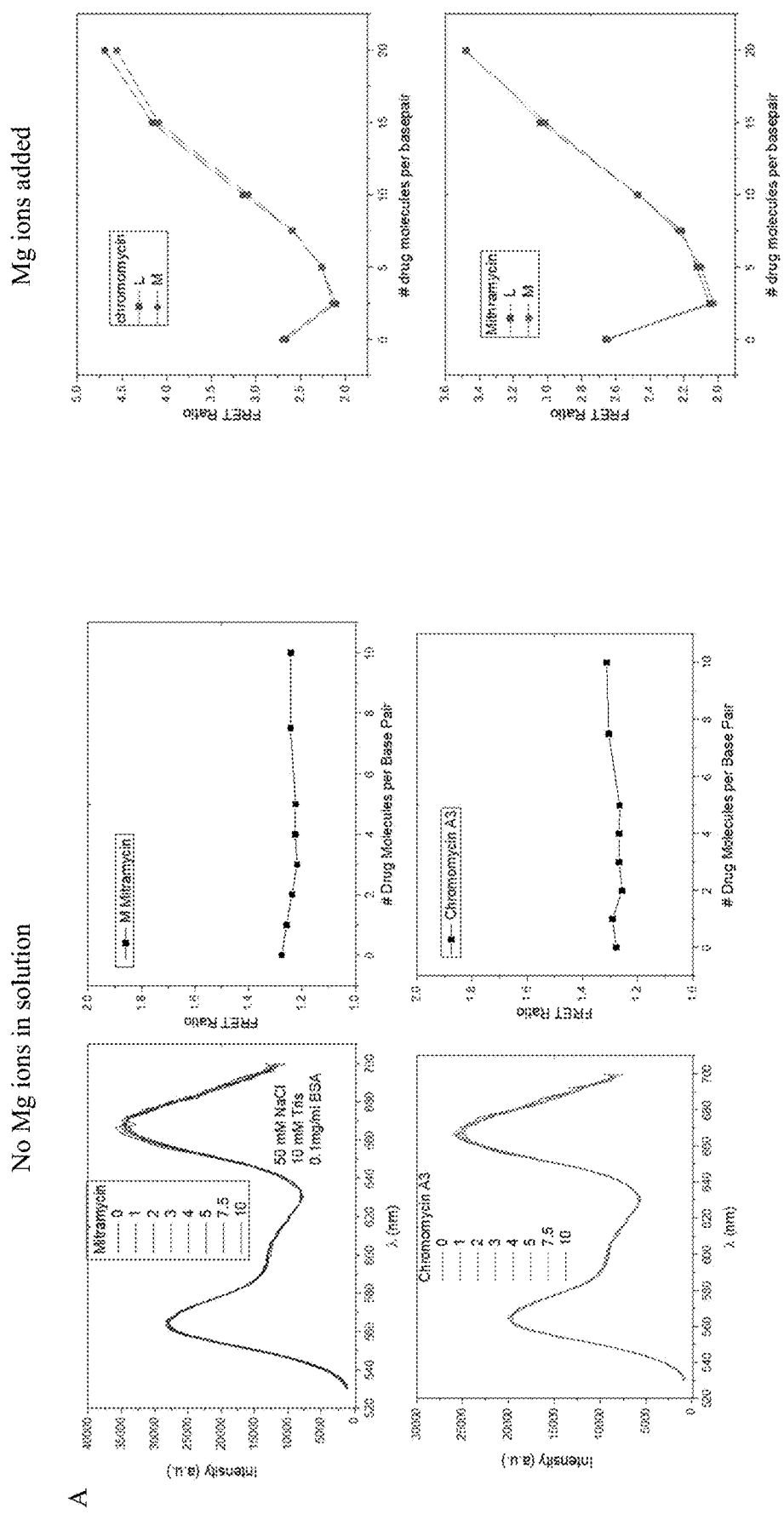
FIG. 27 shows groove binders that need specific ions to bind DNA are detected only in the presence of that ion. (A) This experiment was conducted to demonstrate that the sensor response is elicited only when the molecules bind the DNA and is not a spurious response of the presence of the molecules in solution. For both Mitramycin and Chromomycin, it is known that they need to associate with Magnesium ions before they can bind DNA. Therefore, in the absence of Mg there is no change in the FRET ratio of the sensor when the drug concentration is increased (left, spectra and flat FRET ratio). The response, is however very strong when 20 mM MgCl is added to solution. The FRET ratio increases as a function of drug concentration consistent with groove-binding. Given that Mg ions themselves can shield the DNA, the initial drop in the FRET ratio can be explained by the drug molecules sequestering the Mg ions resulting in the arms of the sensor opening (the right curves are two measurements). (B) shows that while Magnesium alone increases the FRET ratio as expected for electrostatic shielding, the presence of the drug (20 molecules/bp) elicits an even larger increase in the FRET ratio.
Figure 27:
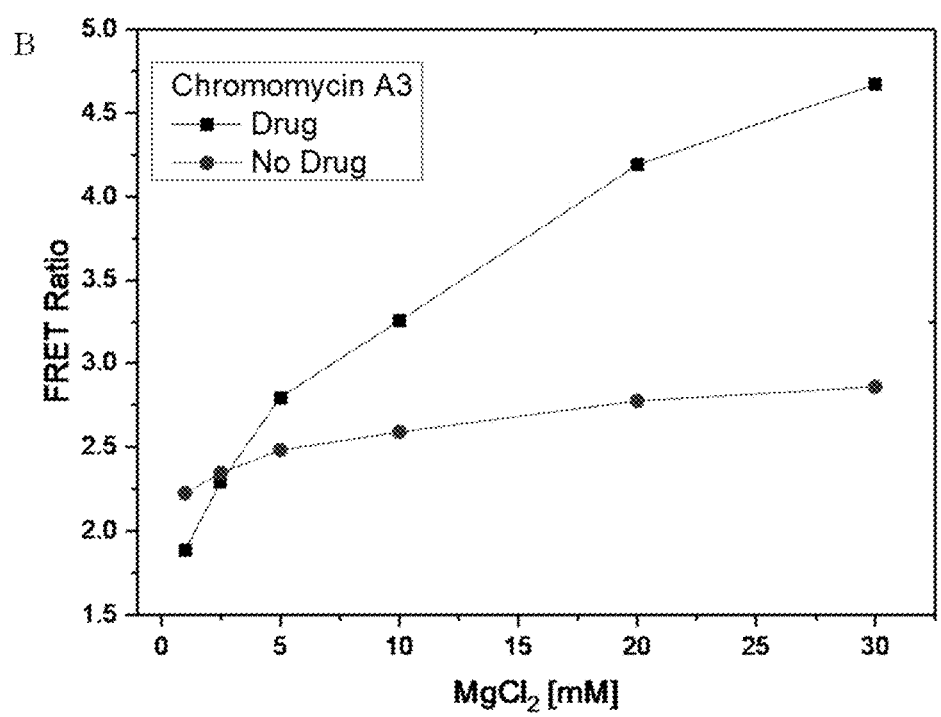
Figure 28:
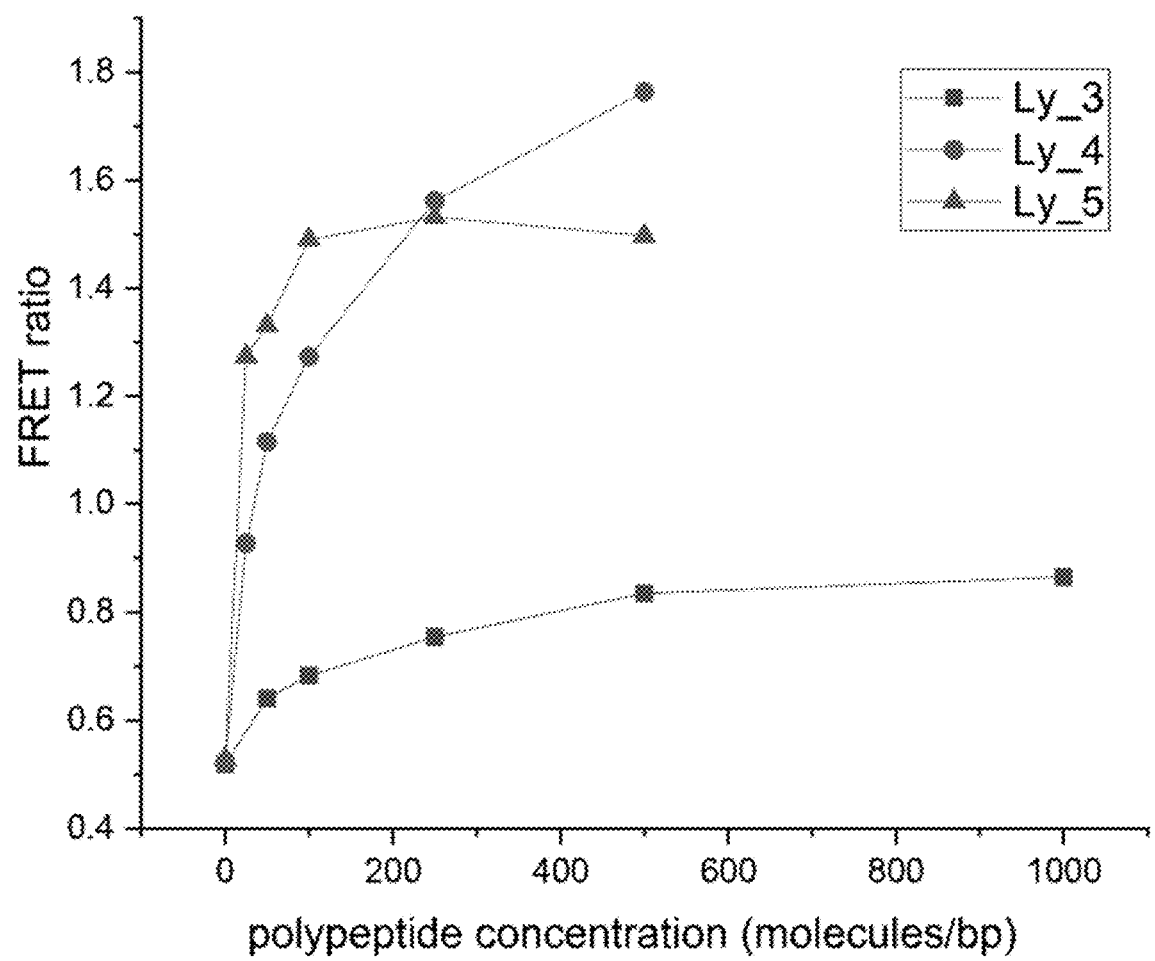
FIG. 28 shows sensors of the present disclosure can detect polypeptides that interact electrostatically with DNA. Tri-lysine (Ly-3), tetra-lysine (Ly-4), and penta-lysine (Ly-5) increase the FRET ratio of the sensor in a concentration-dependent manner consistent with their electrostatic interaction with the DNA. The response of the flexible sensor is steeper for the longer polypeptide having a larger charge density per molecule.

FIG. 25 shows the arms of the flexible molecular sensor get closed with increased electrostatic screening. FIG. 26 shows groove-binding compounds are detected by the flexible molecular sensor as a concentration-dependent increase of the FRET ratio. FIG. 27 shows groove binders that need specific ions to bind DNA are detected only in the presence of that ion. FIG. 28 shows sensors of the present disclosure can detect polypeptides that interact electrostatically with DNA.

Although the present disclosure has been described with respect to one or more particular embodiments and/or examples, it will be understood that other embodiments and/or examples of the present disclosure may be made without departing from the scope of the present disclosure.

The invention claimed is:

1. A method for detecting binding of a substrate to a molecular sensor, wherein the substrate is a small molecule, the method comprising:
   i) contacting in a medium the substrate with the molecular sensor;
   ii) measuring a change in fluorescence of the molecular sensor relative to a reference fluorescent value of the molecular sensor in the absence of the substrate,
wherein the change in fluorescence is indicative of binding of the substrate to the molecular sensor, the binding of the substrate is an intercalation binding event, a major groove binding event, a minor groove binding event, or a combination thereof, and the molecular sensor comprises:
   a) a continuous sequence of DNA having a plurality of portions of complementarity such that the sensor forms a first double-stranded oligonucleotide arm, a second double-stranded oligonucleotide arm, and a linking moiety, wherein the first double-stranded oligonucleotide arm and the second double-stranded oligonucleotide arm are connected by the linking moiety; the first double-stranded oligonucleotide arm comprises a first fluorescent group attached thereto; and the second double-stranded oligonucleotide arm comprises a second fluorescent group attached thereto, wherein the first fluorescent group and the second fluorescent group are disposed on their respective oligonucleotide arms such that the first fluorescent group and the second fluorescent group can interact; or
   b) a double-stranded oligonucleotide, wherein each 5' end has a fluorescent group attached thereto.

2. The method of claim 1, wherein the method is performed on a test sample comprising an analyte of interest.

3. The method of claim 1, wherein the method is performed in vivo.

4. The method of claim 1, wherein the method is performed in vitro.

5. The method of claim 1, wherein the change in fluorescence is caused by a change in spatial separation of a FRET pair.

6. The method of claim 1, wherein the change in fluorescence is caused by interaction of the substrate and the first fluorescent group or second fluorescent group.

7. The method of claim 1, wherein the method further comprises determining if the substrate reached an organelle or cellular structure of interest.

8. The method of claim 1, further comprising determining a distance between the first fluorescent group and the second fluorescent group or the first fluorescent group and/or second fluorescent group and the substrate.

* * * * *